United States Patent
Sauder

(10) Patent No.: US 10,620,185 B2
(45) Date of Patent: *Apr. 14, 2020

(54) MOLECULAR BARCODED BI-STABLE SWITCH

(71) Applicant: Timothy Lee Sauder, Palo Alto, CA (US)

(72) Inventor: Timothy Lee Sauder, Palo Alto, CA (US)

(73) Assignee: APTASCAN, INC., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/832,113

(22) Filed: Dec. 5, 2017

(65) Prior Publication Data

US 2018/0095068 A1    Apr. 5, 2018

Related U.S. Application Data

(63) Continuation-in-part of application No. 15/053,228, filed on Feb. 25, 2016, now Pat. No. 9,863,930.

(60) Provisional application No. 62/121,709, filed on Feb. 27, 2015.

(51) Int. Cl.
    *G01N 33/487*  (2006.01)
    *G01N 27/447*  (2006.01)
    *G01N 33/53*   (2006.01)
    *G01N 33/543*  (2006.01)

(52) U.S. Cl.
    CPC . *G01N 33/48721* (2013.01); *G01N 27/44791* (2013.01); *G01N 33/5308* (2013.01); *G01N 33/54366* (2013.01)

(58) Field of Classification Search
    CPC ............. G01N 33/48721; G01N 27/44791
    See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 2008/0293160 A1 | 11/2008 | Sen et al. |
| 2010/0331194 A1 | 12/2010 | Turner |
| 2013/0224859 A1 | 8/2013 | Bachelet et al. |
| 2013/0261019 A1 | 10/2013 | Lin et al. |

FOREIGN PATENT DOCUMENTS

| | | |
|---|---|---|
| WO | 9638553 A1 | 12/1996 |
| WO | 2014072703 A1 | 5/2014 |
| WO | 2014144744 A1 | 9/2014 |

OTHER PUBLICATIONS

Lin et al, Self-Assembled Combinatorial Encoding Nanoarrays for Multiplexed Biosensing, 2007, Nano Lett., 7, 507-512.
Lin et al, Self-Assembled Combinatorial Encoding Nanoarrays for Multiplexed Biosensing, 2007, Nano Lett., 7, 507-512. Supplemental information, pp. 1-6.
Darlsen et al., Selective Detection and Quantification of Modified DNA with Solid-State Nanopores, Nano Letters, 2014, 14 (10), pp. 5488-5492.
Howarth et al., A monovalent streptavidin with a single femtomolar biotin binding site Nat Methods. Apr. 3, 2006 A):267-73.
3A1 et al., Cryo-EM structure of a 3D DNA-origami object, H PNAS 2012 109 (49) 20012-20017.
Douglas et al., Rapid prototyping of 3D DNA-origami shapes with caDNAno, Nucl_ Acids Res. (2009) 37 (15): 5001-5006.

*Primary Examiner* — Narayan K Bhat
(74) *Attorney, Agent, or Firm* — William A. Ziehler; Shumaker, Loop & Kendrick, LLP

(57) ABSTRACT

Various molecular barcoded bi-stable switches are provided that can be used to detect various analytes. An electrical current is provided through a pore to electrophoretically draw at least a portion of one or more molecular barcoded bi-stable switches from one volume through one or more pores to another volume. Each molecular barcoded bi-stable switch includes a status identifier that provides an indication when a binding material is bound to the analyte. Each molecular barcoded bi-stable switch also includes a barcode that can be read as it passes through the pore to ascertain the identity of the particular molecular barcoded bi-stable switch.

29 Claims, 14 Drawing Sheets

MOLECULAR BARCODED BI-STABLE SWITCH

CROSS-REFERENCE TO RELATED APPLICATIONS

This application is a continuation-in-part of U.S. patent application Ser. No. 15/053,228, filed on Feb. 25, 2016, and claims the benefit of U.S. Provisional Application No. 62/121,709, filed on Feb. 27, 2015. The entire disclosures of the above applications are incorporated herein by reference.

FIELD

The present technology relates to a barcoded and bi-stable molecular switch, including a molecular switch having binding functionality, such as an aptamer, for detecting an analyte and a molecular barcode particular to the switch.

INTRODUCTION

This section provides background information related to the present disclosure which is not necessarily prior art.

Various materials exhibit a selective affinity for each other that can result in formation of a bi-molecular or multi-molecular complex, such as receptor-ligand, antibody-antigen, and aptamer-target interactions. Selective affinity of one material for another, such as an affinity for a particular analyte of interest, can be used to determine the presence of the analyte in a given sample medium and can be used to determine the concentration of the analyte in certain circumstances. Various detection methodologies can be used to ascertain complex formation between a material and an analyte of interest, including direct and indirect detection strategies to detect and/or amplify signals related a primary binding event or secondary binding events, where binding measurements can utilize one or more spectroscopic, colorimetric, and fluorescent signals, for example. Certain materials, such as aptamers, can be engineered to have a selective affinity for a particular analyte of interest and allow for customized detection of analytes where no natural or practical binding partners exist.

Aptamers are oligonucleotides or peptides which can be used as an analytical tool to detect and quantify a broad array of targets, such as medications, nutrients, hormones, neurotransmitters, and many other chemical and biological signals. Various aptamers can be optimized to bind to a particular target or analyte with high affinity and specificity using one or more synthetic evolutionary processes. Aspects of these processes were developed nearly two decades ago and have since been refined and improved extensively; e.g., nucleic acid aptamers described by U.S. Pat. Nos. 5,270,163 and 5,475,096 to Gold et al. and peptide aptamers described by WO1996038553 A1 to Dalum et al. Once an aptamer is developed for a certain analyte, it can be used as an alternative to antibodies, including monoclonal antibodies, in various diagnostic or laboratory tests to measure the presence of the analyte in a given sample.

As with most diagnostic tests, an event, like a single aptamer binding to its respective analyte, is not observed directly. Instead, inside even a tiny droplet of sample, a vast number of such interactions can collectively result in a slight optical shift or color change. This change can be in turn detected using large, complex instruments like spectrophotometers and surface plasmon resonance systems. Aside from the detection method employed, it may be necessary to subject the samples to be analyzed to extensive multistep purification and preparation methods before measurement or analysis using such instruments. In recent years, such instruments have somewhat decreased in size and have become more automated, resulting in marginally improved availability and portability of diagnostic tests. That said, such instrumentation is often nowhere near compact enough or amenable for configuration or packaging to be made portable or even implantable, nor inexpensive enough to be used as a point-of-care diagnostic device, much less as a disposable device. In short, developing different aptamers, including tens, hundreds, or even thousands of different aptamers, each of which binds to its own particular analyte, can be achieved using routine processes and the engineered aptamers produced at relatively low cost. Key issues, however, relate to ways of determining precisely which aptamers and how many aptamers have encountered a respective analyte.

SUMMARY

The present technology includes systems, processes, articles of manufacture, and compositions that relate to bi-stable molecular switches for detecting one or more various analytes.

Molecular barcoded bi-stable switches for various analytes are provided, where each switch includes a body, a barcode, and a bi-stable switch. The bi-stable switch includes a binding material, an anchor, and a status identifier. The binding material has a first affinity for the analyte and a second affinity for the anchor, where the first affinity is greater than the second affinity. The status identifier provides an indication when the binding material is bound to the analyte.

Sensor for detecting various analytes are provided, where each sensor includes a molecular barcoded bi-stable switch as provided herein. A first volume is fluidly connected to a second volume by a pore, where the molecular barcoded bi-stable switch disposed in one of the first volume and the second volume. A first electrode is in electrical communication with the first volume and a second electrode is in electrical communication with the second volume, where the pore permits an electrical current to pass between the first volume and the second volume.

Methods of detecting various analytes are provided, where each method includes a sensor as provided herein. An electrical current is provided through a pore to electrophoretically draw at least a portion of a molecular barcoded bi-stable switch from one of a first volume and a second volume through the pore to the other of the first volume and the second volume. Whether a status identifier is providing an indication that a binding material is bound to the analyte is determined.

Other molecular barcoded bi-stable switches for various analytes are provided, where each switch includes a body, a barcode, and a bi-stable switch. The bi-stable switch includes a binding material, an anchor, and a status identifier. The binding material, the anchor, and the analyte cooperatively bind together. The status identifier provides an indication when the analyte is cooperatively bound with the binding material and the anchor. The binding material can have a first affinity for the analyte and the anchor can have a second affinity for the analyte. The binding material and the anchor can cooperatively bind the analyte with a third affinity, where the third affinity is greater than the first affinity and is greater than the second affinity. The binding material, for example, can have a first affinity for a first epitope of the analyte and the anchor can have a second affinity for a second epitope of the analyte. The analyte can be sandwiched between the binding material and the anchor when the analyte is cooperatively bound with the binding material and the anchor.

Other sensors for detecting various analytes are provided, where each sensor includes a molecular barcoded bi-stable switch as provided herein, including a bi-stable switch having a binding material, an anchor, and a status identifier. The binding material, the anchor, and the analyte cooperatively bind together, where the status identifier provides an indication when the analyte is cooperatively bound with the binding material and the anchor. A first volumn is fluidly connected to a second volume by a pore, where the molecular barcoded bi-stable switch is disposed in one of the first volume and the second volume. A first electrode is in electrical communication with the first volume and a second electrode in electrical communication with the second volume, where the pore permits an electrical current to pass between the first volume and the second volume.

Other methods of detecting various analytes are provided, where each method includes a sensor as provided herein. The sensor includes a bi-stable switch having a binding material, an anchor, and a status identifier. The binding material, the anchor, and the analyte cooperatively bind together, where the status identifier provides an indication when the analyte is cooperatively bound with the binding material and the anchor. An electrical current is provided through a pore to electrophoretically draw at least a portion of a molecular barcoded bi-stable switch from one of a first volume and a second volume through the pore to the other of the first volume and the second volume. Whether a status identifier is providing an indication that a binding material is bound to the analyte is determined.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

The reference numerals depicted in the accompanying figures of this provisional application are particular to each figure and are not representative of identical or similar elements between different figures.

DETAILED DESCRIPTION

Figure 1:
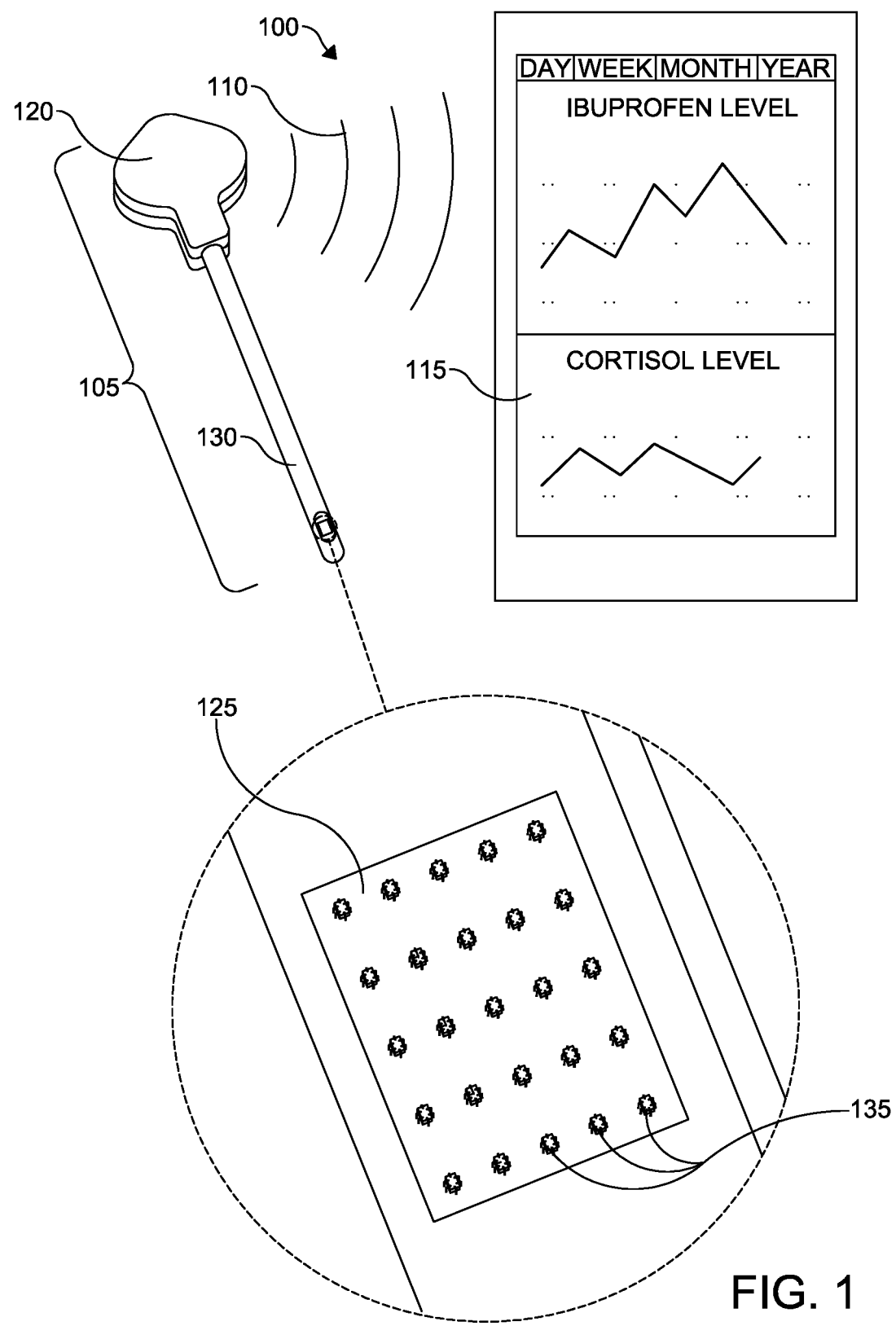
FIG. 1 depicts an embodiment of a system including a sensor.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. Except where otherwise expressly indicated, all numerical quantities in this description are to be understood as modified by the word "about" and all geometric and spatial descriptors are to be understood as modified by the word "substantially" in describing the broadest scope of the technology. All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of" Thus, for any given embodiment reciting materials, components, or process steps, the present technology also specifically includes embodiments consisting of, or consisting essentially of, such materials, components, or process steps excluding additional materials, components, or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology relates to various molecular barcoded bi-stable switches, various sensors for detecting an analyte that include one or more molecular barcoded bi-stable switches, and various methods of detecting an analyte using one or more molecular barcoded bi-stable switches. Synthetic and natural components can be configured to provide macromolecular constructs with various functionalities for detecting various analytes. In particular, structure-based design principles are combined with particular molecular interactions and properties. Various physical, chemical, and electrical properties of these engineered macromolecules are utilized to provide rapid and sensitive detection means for one or more analytes of interest.

Engineering and fabrication technologies are being successfully applied at ever smaller scales. At the same time, synthesis and construction methods for various molecules and molecular complexes, including various biomolecules and polymers, are being successfully applied at ever larger scales. These engineering, synthesis, and design principles are now coming together to permit fabrication of devices that include various molecular machines, including various molecular switches, circuits, and other components. Continuing developments in semiconductor device fabrication technology, in particular, have resulted in devices with increasingly smaller features. For example, semiconductors with features 22 nm in size are commercially available. Likewise, it is now possible to synthesize and engineer biomolecules that are vastly larger than anything organic chemists could previously construct. One such example includes certain nucleic acid structures, dubbed "DNA origami," that can be engineered on the order of tens to hundreds of nanometers in size. The overlap in scale and engineering expertise facilitates the construction of the present technology.

A molecular barcoded bi-stable switch for an analyte can include a body, a barcode, and a bi-stable switch. The bi-stable switch can include a binding material, an anchor, and a status identifier. The binding material can have a first affinity for the analyte and can have a second affinity for the anchor. The first affinity can be greater than the second affinity. For example, the binding material can exhibit a stronger interaction with the analyte and have a greater propensity to remain complexed with the analyte in comparison to the anchor. The second affinity, however, can result in the binding material being bound to the anchor in the absence of the analyte. Affinity can be the result of various ionic bonds, hydrogen bonds, and/or van der Waals forces between the binding material and the analyte or between the binding material and the anchor. The status identifier can provide an indication when the binding material is bound to the analyte.

The body of the molecular barcoded bi-stable switch can include an elongate member. For example, the body can be configured as an elongate or rod-like member having two ends separated by an intermediate portion. For example, the body can have an aspect ratio of length:thickness of 2:1 or more. Further examples include aspect ratios of length:thickness ranging from 2:1 to 30:1, including 5:1, 10:1, 15:1, 20:1, 25:1, and so on up to 400:1. The body can include various synthetic or natural molecules, including various macromolecules and biomolecules. In certain embodiments, the body can include a nucleic acid polymer, including single-stranded or double-stranded nucleic acids such as RNA and DNA. Other examples of the body include various linear polymers, including proteins, and synthetic constructs such as carbon nanotubes and other like structures.

The barcode of the molecular barcoded bi-stable switch can include a plurality of molecules coupled to the body. The plurality of molecules coupled to the body can provide a spatial pattern unique to the molecular barcoded bi-stable switch. For example, the plurality of molecules coupled to the body can provide a 2 of 5 interleaved barcode pattern encoding a six digit number, although other types of spatial patterns can be employed. The plurality of molecules forming the barcode can include proteins, including proteins that bind to certain nucleic acid sequences, for example.

The binding material of the bi-stable switch can be selected or engineered based on the analyte of interest. For example, many natural and synthetic molecular complexes exist, where if the analyte of interest is known to form a complex with one or more other entities, these one or more other entities can be used as the binding material. The binding material and analyte can therefore embody various interactions between small molecules, receptor-ligands, antibody-antigens, aptamer-targets, etc. For example, the binding material can be a receptor and the analyte a ligand to the receptor, the binding material can be an antibody and the analyte an antigen, the binding material can be an aptamer and the analyte a target against which the aptamer was selected.

In certain cases, the binding material can be used to indirectly bind the analyte of interest. Such a situation exists where one of the binding material and the analyte recognizes an intermediary material that binds the other of the binding material and the analyte. For example, the binding material and the analyte of interest may both bind to the intermediary material, where the intermediary material acts as a bridge between the binding material and the analyte. Alternatively, either the binding material or the analyte can be coupled to the intermediary material; e.g., by a covalent tether, cross-linking, disulfide bond, among others. Examples include where the analyte of interest is coupled to biotin and the binding material includes streptavidin, the analyte is coupled to digoxigenin and the binding material includes an anti-digoxigenin antibody, among others.

The anchor of the bi-stable switch can be a material having lower binding affinity for the binding material than the analyte. That is, the binding constant of the analyte to the binding material can be greater than the binding constant of the anchor to the binding material. Put another way, the dissociation constant of the analyte from the binding material can be less than the dissociation constant of the anchor from the binding material. Where the analyte is present, the binding material can spend more time bound to the analyte than to the anchor. In certain cases, the binding material can have a dissociation constant with the analyte that is one or more orders of magnitude lower than a dissociation constant with the anchor. The anchor can include a partial analyte structure or an analyte that is modified in some manner to reduce its affinity for the binding material. The anchor can also interact with the binding material in a manner different from how the analyte interacts with the binding material. For example, the anchor can interact with the binding material at a different site than the analyte and/or through a different combination of interactions, including ionic bonds, hydrogen bonds, and/or van der Waals forces. Where the binding material includes an aptamer, for example, the anchor can include a nucleic acid strand having partial complementarity to the aptamer. This can allow the bi-stable switching portion to be stabilized by blunt-ended nucleic acid stacking interactions when the aptamer is bound to the anchor, where the blunt-ended nucleic acid stacking interactions are inhibited when the aptamer is bound to the analyte.

As noted, the status identifier of the bi-stable switch can provide an indication when the binding material is bound to the analyte. The indication can be a structural or conformational change in the status identifier and/or a structural, conformational, and/or positional change in the status identifier relative to another portion of the molecular barcoded bi-stable switch. The indication can be a structural or conformational change that results in a change of position of the status identifier relative to a remainder of the barcode when the binding material is bound to the analyte. For example, the status identifier can provide an indication that modifies the barcode, where the modification can include an additional signal relative to the barcode or removal of a signal relative to the barcode of the molecular barcoded bi-stable switch.

As described, the analyte and the anchor can compete with each other to bind to the binding material. When the analyte is present, the analyte can win this competition and the binding material can spend a majority of the time bound to the analyte. However, in certain embodiments, the analyte, anchor, and binding material can cooperatively bind together. Cooperative binding of the analyte, anchor, and binding material can provide a change with respect to the status identifier to provide the indication when the analyte, anchor, and binding material are cooperatively bound. For example, the cooperative binding can form a complex that provides a structural change in the status identifier, indicating formation and presence of the analyte, anchor, and binding material complex. An example of such cooperative binding is described in International Publication No. WO 2014/144744 A1 to Stojanovic et al. and U.S. application Ser. No. 14/855,171, which claim priority to U.S. Provisional Application No. 61/798,079. Formation of the analyte, anchor, and binding material complex can increase specificity and affinity for the analyte. In the absence of the analyte, the binding material and anchor can have very low affinity for each other. The bistable switch can be stabilized in the absence of bound analyte by a stabilizing element or catch strand. For example, the stabilizing element or catch strand can have a second affinity for the anchor, and can be located opposite the binding material on the bistable switch.

The molecular barcoded bi-stable switch can further include a stopper. The stopper can have a dimension configured to prevent the stopper from passing through a pore or or other passageway, thereby preventing the entirety of the molecular barcoded bi-stable switch from passing therethrough. For example, the stopper can have a first dimension and the barcode of the molecular barcoded bi-stable switch can have a second dimension, where the first dimension is greater than the second dimension. In this way, the stopper can have a first dimension configured to prevent the stopper from passing through the pore or passageway whereas the barcode can have a second dimension configured to allow the barcode portion of the molecular barcoded bi-stable switch to pass through the pore or passageway. Where the body of the molecular barcoded bi-stable switch includes an elongate member having a first end, an intermediate portion, and a second end, the bi-stable switch can be coupled to the first end, the barcode can be coupled to the intermediate portion, and the stopper can be coupled to the second end. The stopper can include various materials of appropriate dimension and size to prevent passage through a given pore or passageway. For example, where the body includes an elongate member, the elongate member can have a certain average dimension or diameter that is able to fit through the pore or passageway, whereas the stopper coupled to one of the ends of the elongate member has a certain average dimension or diameter that prevents the stopper, and hence the entire molecular barcoded bi-stable switch, from passing through the pore or passageway. The stopper can include one or more nucleic acid binding proteins when the body includes an elongate member formed of nucleic acid. The stopper can also include various natural and synthetic materials, polymers, macromolecules, and structures formed thereby. For example, the stopper can be configured as a nanoscale particle or bead or a microscale particle or bead, based on the size and nature of the pore or passageway and the scale necessary to prevent the stopper from passing therethrough.

The molecular barcoded bi-stable switch can include a portion that is electrically charged. This property allows the molecular barcoded bi-stable switch to be responsive to an electric field and subject to electrophoresis. The electrically charged portion can be positively charged or negatively charged. The electrically charged portion can include the body of the molecular barcoded bi-stable switch; for example, where the body comprises a nucleic acid. The electrically charged portion of the molecular barcoded bi-stable switch can also be one or more materials that are bound or coupled to the molecular barcoded bi-stable switch. For example, various electrically charged polymers and structures formed of such polymers (e.g., beads or particles), as well as various coordinated or associated metal ions.

In certain embodiments, the various aspects of the present technology can be used to form a molecular barcoded bi-stable switch for an analyte that comprises a body, a barcode, a bi-stable switch, and a stopper. The body can include an elongate member having a first end, an intermediate portion, and a second end. The barcode can be coupled to the first end of the elongate member and can include a plurality of molecules coupled to the intermediate portion of the elongate member that provide a spatial pattern unique to the molecular barcoded bi-stable switch. The bi-stable switch can be coupled to the first end of the elongate member and can include a binding material, an anchor, and a status identifier. The binding material can have a first affinity for the analyte and a second affinity for the anchor, where the first affinity can be greater than the second affinity. The binding material can include an aptamer. The anchor can include a nucleic acid strand having partial complementarity to the aptamer. The bi-stable switching portion can be stabilized by blunt-ended nucleic acid stacking interactions when the aptamer is bound to the anchor and the blunt-ended nucleic acid stacking interactions can be inhibited when the aptamer is bound to the analyte. The status identifier can provide an indication when the binding material is bound to the analyte, where the indication can include a position change of the status identifier relative to the barcode when the binding material is bound to the analyte. The stopper can be coupled to the second end of the elongate member. The stopper can have a first dimension and the barcode can have a second dimension, where the first dimension is greater than the second dimension.

A sensor for detecting an analyte can include a molecular barcoded bi-stable switch as described herein, a first volume fluidly connected to a second volume by a pore, a first electrode in electrical communication with the first volume, and a second electrode in electrical communication with the second volume. The molecular barcoded bi-stable switch can be disposed in one of the first volume and the second volume. The pore can permit an electrical current to pass between the first volume and the second volume. The barcode can be configured to change the electrical current when the barcode passes through the pore. When the molecular barcoded bi-stable switch includes a stopper, the stopper can be configured to reduce the electrical current when the stopper at least partially occludes the pore.

The sensor can include various numbers and types of molecular barcoded bi-stable switches arranged in various shared and discrete volumes, including various discrete volumes that are fluidly connected to other discrete volumes or are fluidly connected to a common shared volume. The sensor can include a plurality of the molecular barcoded bi-stable switches. The plurality of molecular barcoded bi-stable switches can include a plurality of different molecular barcoded bi-stable switches each having a different barcode and each having a different binding material with a different first affinity for a different analyte. The sensor can also include a plurality of the first volumes fluidly connected to a plurality of the second volumes by a plurality of pores. The sensor can also include a plurality of first electrodes and a plurality of second electrodes. A respective one of the first electrodes can be in electrical communication with a respective one of the first volumes. A respective one of the second electrodes can be in electrical communication with a respective one of the second volumes. A respective one of the pores can permit an electrical current to pass between the respective one of the first volumes and the respective one of the second volumes. Various sensors can further include where the plurality of molecular barcoded bi-stable switches includes a plurality of different molecular barcoded bi-stable switches each having a different barcode and each having a different binding material with a different first affinity for a different analyte. Different molecular barcoded bi-stable switches can be disposed in one of the respective first volumes and the respective second volumes.

The various volumes in the sensor, including the one or more first volumes and the one or more second volumes, can embody various fluid amounts. These volumes can range from milliliters to microliters to nanoliters. For example, a volume in which one or more molecular barcoded bi-stable switches are disposed can range from microliters to nanoliters. In certain embodiments, the volume in which one or more molecular barcoded bi-stable switches are disposed can be from 1 to 10 nanoliters, where the corresponding volume fluidly connected by the pore can be larger. For example, a sample volume to be analyzed for one or more analytes can be on the order of milliliters or microliters of fluid whereas the volume(s) across the pore(s) containing the one or more molecular barcoded bi-stable switches may only include nanoliters of fluid.

A method of detecting an analyte can include a sensor as described herein, where an electrical current is provided through the pore to electrophoretically draw at least a portion of the molecular barcoded bi-stable switch from one of the first volume and the second volume through the pore to the other of the first volume and the second volume. The method can further include determining whether the status identifier is providing the indication that the binding material is bound to the analyte. The method can also include reading the barcode as the barcode passes through the pore. For example, changes in the electrical current related to the barcode passing through the pore can identify a particular molecular barcoded bi-stable switch. One or more ammeters can be configured with one or more sensors in reading the respective barcodes as well as the status identifiers. The method can further include reversing the electrical current through the pore to electrophoretically draw at least a portion of the molecular barcoded bi-stable switch to the one of the first volume and the second volume through the pore from the other of the first volume and the second volume. For example, a molecular barcoded bi-stable switch can be electrophoretically drawn from a volume in a sensor cell through a pore into a sample volume where it may encounter one or more analytes. As the molecular barcoded bi-stable switch is drawn through the pore, the status identifier alone or in relation to the barcode can identify the particular molecular barcoded bi-stable switch. Once the electrical current is reversed, any molecular barcoded bi-stable switch with bound analyte is drawn back through the pore into the sensor cell and can provide the indication of binding material bound with analyte using the status identifier.

The present technology further includes the following variations with respect to the molecular barcoded bi-stable switches, sensors, and methods already described herein. It is noted that the following aspects and variations can be used in combination with or in place of various aspects and features of the preceding molecular barcoded bi-stable switches, sensors, and methods. In certain instances, one or more of the following aspects and variations relate to molecular barcoded bi-stable switches, sensors, and methods or portions thereof as already described herein.

A molecular barcoded bi-stable switch for an analyte can include a body, a barcode, a stopper, and a bi-stable switch. The body can include an elongate member. The stopper can have a first dimension relative a diameter of the elongate member, the barcode can have a second dimension relative to the diameter of the elongate member, where the first dimension is greater than the second dimension. The bi-stable switch can include a binding material, an anchor, and a status identifier. The binding material, the anchor, and the analyte can cooperatively bind together, where the status identifier can provide an indication when the analyte is cooperatively bound with the binding material and the anchor. The indication can be provided with the status identifier coupled to the body.

In certain embodiments, the binding material can have a first affinity for the analyte and the anchor can have a second affinity for the analyte. This can allow the binding material and the anchor to cooperatively bind the analyte with a third affinity, where the third affinity can be greater than the first affinity and can be greater than the second affinity. The binding material can also have a first affinity for a first epitope of the analyte and the anchor can also have a second affinity for a second epitope of the analyte. The analyte can be substantially sandwiched between the binding material and the anchor when the analyte is cooperatively bound with the binding material and the anchor.

The stopper can include one of a particle and a bead. The particle or the bead can provide the first dimension relative to the diameter of the elongate member. The stopper can also include a magnetic component, such as a magnetic bead. The molecular barcoded bi-stable switch can also a portion that is electrically charged. In some embodiments, the stopper includes a magnetic bead and the molecular barcoded bi-stable switch includes a portion that is electrically charged. Where the body of the molecular barcoded bi-stable switch comprises a nucleic acid polymer, the nucleic acid polymer can be electrically charged.

As mentioned, the barcode can include a plurality of molecules coupled to the body that provide a spatial pattern unique to the molecular barcoded bi-stable switch. However, the barcode can also include one or more narrow regions of the elongate member and one or more wide regions of the elongate member, where the one or more narrow regions have a diameter less than the one or more wide regions. The one or more wide regions can have a diameter that is not wider than the diameter of the elongate member. In this way, the narrow region(s) and the wide region(s) can provide a spatial pattern unique to the molecular barcoded bi-stable switch. The status identifier can alter the spatial pattern when the binding material, the anchor, and the analyte cooperatively bind together. For example, the indication provided by the status identifier can include a position change of the status identifier relative to a remainder of the barcode when the binding material, the anchor, and the analyte are cooperatively bound together.

A sensor for detecting an analyte can include a molecular barcoded bi-stable switch for the analyte, a first volume, a second volume, a pore, a first electrode, and a second electrode. The molecular barcoded bi-stable switch for the analyte can include a body, a barcode, and a bi-stable switch. The bi-stable switch can include a binding material, an anchor, and a status identifier, where the binding material, the anchor, and the analyte cooperatively bind together. The status identifier provides an indication when the analyte is cooperatively bound with the binding material and the anchor, where the indication is provided with the status identifier coupled to the body. The first volume is fluidly connected to the second volume by the pore. The molecular barcoded bi-stable switch is disposed in one of the first volume and the second volume. The first electrode is in electrical communication with the first volume and the second electrode is in electrical communication with the second volume, the pore permitting an electrical current to pass between the first volume and the second volume.

With respect to the sensor, the barcode can be configured to change the electrical current when the barcode passes through the pore. The sensor can also include a plurality of the molecular barcoded bi-stable switches, where the plurality of the molecular barcoded bi-stable switches can include identical molecular barcoded bi-stable switches or different molecular barcoded bi-stable switches. The plurality of molecular barcoded bi-stable switches, for example, can include a plurality of different molecular barcoded bi-stable switches each having a different barcode and each having a different binding material with a different first affinity for a different analyte. The sensor can also have a plurality of the first volumes fluidly connected to a plurality of the second volumes by a plurality of pores. There can be a plurality of first electrodes, where a respective one of the first electrodes is in electrical communication with a respective one of the first volumes, and a plurality of second electrodes, where a respective one of the second electrodes is in electrical communication with a respective one of the second volumes, and a respective one of the pores permitting an electrical current to pass between the respective one of the first volumes and the respective one of the second volumes. The sensor can further include a plurality of the molecular barcoded bi-stable switches and the plurality of molecular barcoded bi-stable switches can include a plurality of different molecular barcoded bi-stable switches each having a different barcode and each having a different binding material with a different first affinity for a different analyte, and different molecular barcoded bi-stable switches are disposed in one of the respective first volumes and the respective second volumes. The first volume and the second volume can each include about 1 nanoliter of a liquid. The molecular barcoded bi-stable switch in the sensor can further include a stopper as described, where the stopper can be configured to reduce the electrical current when the stopper at least partially occludes the pore.

A method of detecting an analyte can include providing a sensor for detecting an analyte, where the sensor can include the various sensors described herein. An electrical current is provided through the pore of the sensor to electrophoretically draw at least a portion of the molecular barcoded bi-stable switch of the sensor from one of the first volume of the sensor and the second volume of the sensor through the pore of the sensor to the other of the first volume of the sensor and the second volume of the sensor. The analyte is detected when the indication of the molecular barcoded bi-stable switch of the sensor includes a position change of the status identifier relative to a remainder of the barcode when the binding material is bound to the analyte. The barcode of the molecular barcoded bi-stable switch can be read as the barcode passes through the pore. The electrical current through the pore can be reversed to electrophoretically draw at least a portion of the molecular barcoded bi-stable switch to the one of the first volume and the second volume through the pore from the other of the first volume and the second volume.

With reference now to FIGS. 1-14, non-limiting examples of the present technology are described.

FIG. 1 shows an embodiment of a system 100 including a sensor 105 according to the present technology. This embodiment includes a sensor 105 that can be used in practice very much like a conventional oral thermometer, ubiquitous to healthcare providers and patients everywhere. However, in lieu of or in addition to merely displaying temperature, the sensor 105 is capable of making one or more realtime measurements of a complex array of analytes including biomarkers, medications, nutrients, hormones, neurotransmitters, and other biological signals present in a patient's saliva. Given the substantial amount of data the sensor 105 produces, the sensor 105 can transmit 110 measurements in realtime to another device 115, such as a mobile device, for display and analysis, where transmission can be wirelessly effected via a secure Bluetooth™ wireless link, for example. A polymer housing 120 at base of the sensor 105 can contain a coin cell battery, signal processing circuitry, and a wireless transceiver (e.g., BlueTooth™ LE transceiver).

The inset of FIG. 1 shows a detailed view of a sensor surface 125. The sensor surface 125 can be encapsulated near the tip of the sensor's tubular stainless steel shank 130 with the sensor surface 125 exposed to the sensor's surroundings, which in this embodiment includes the patient's saliva and/or mucous membranes. This sensor surface 125 features one or more nano-pore cells 135, such as an array of nano-pore cells 135, which are shown in further detail in subsequent figures.

Figure 2:
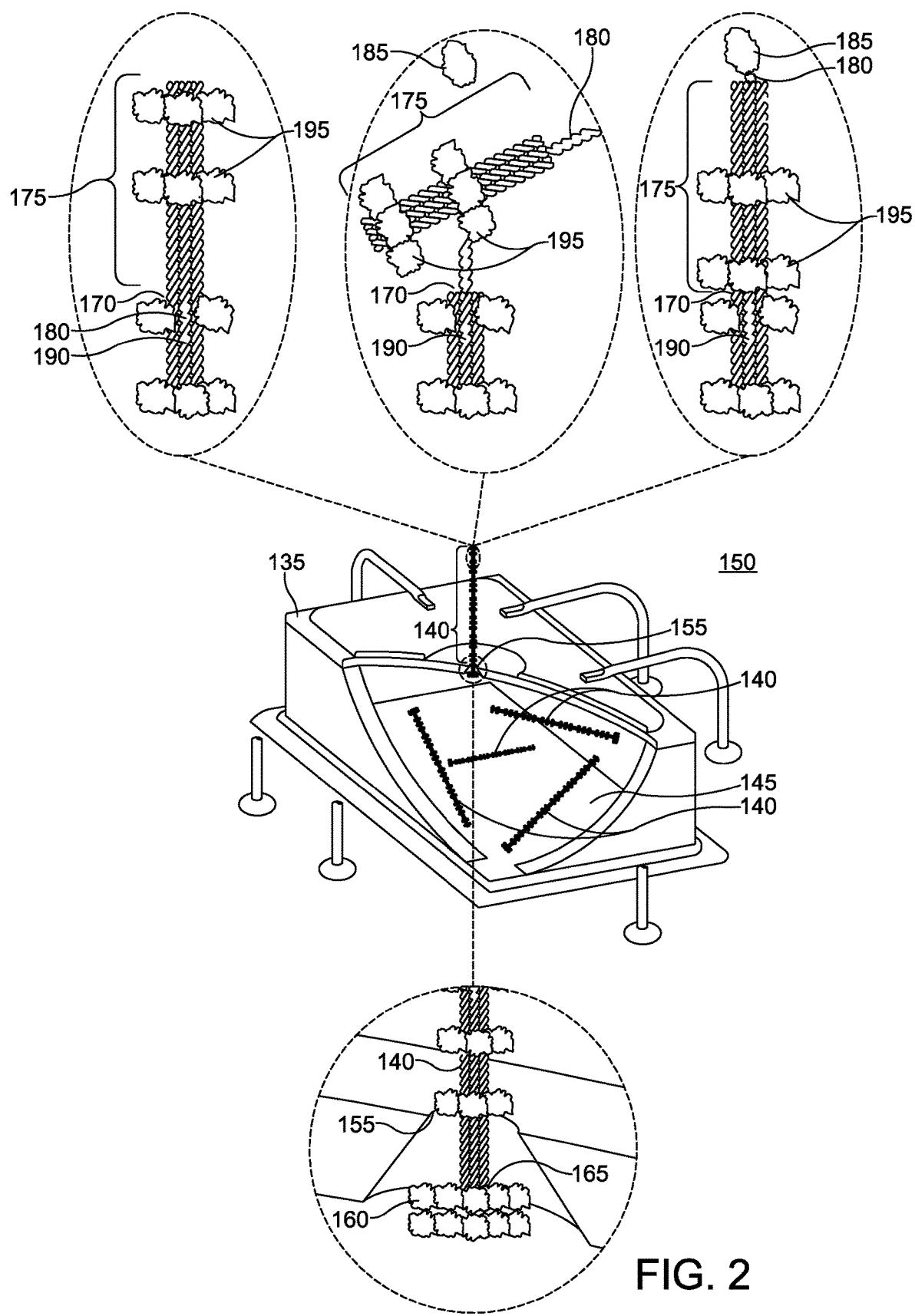
FIG. 2 depicts an embodiment of the sensor including a molecular barcoded bi-stable switch for an analyte, where a binding material switches between interaction with an anchor and interaction with the analyte.

FIG. 2 shows a single nano-pore cell 135 that can contain approximately 1 nanoliter of solution of molecular barcoded bi-stable switches 140. Assuming a 20 nanomole (nmol) concentration of molecular barcoded bi-stable switches 140, a single nano-pore cell 135 shown here contains about 12 million molecular barcoded bi-stable switches. An interior 145 (or first volume) of the nano-pore cell 135 is separated from an exterior 150 of the nano-pore cell 135 by a nano-pore 155. A single molecular barcoded bi-stable switch 140 is shown extending from the interior 145 of the nano-pore cell 135 to the exterior 150 of the nano-pore cell 135 through the nano-pore 155. A stopper 160 at one end 165 of the molecular barcoded bi-stable switch 140 prevents the molecular barcoded bi-stable switch 140 from passing through the nano-pore 155 and to the exterior 150 of the nano-pore cell 135. On the other end 170 of the molecular barcoded bi-stable switch 140 is a bistable switch 175 which is driven by Brownian motion between two stable orientations, shown in detail in the left and right panels of the bottom inset of FIG. 2. Blunt-ended DNA stacking interactions stabilize the bistable switch 175 in either of the two orientations. Extending from one end of the bistable switch 175 is an aptamer 180 functioning as a binding material that has a first affinity for an analyte 185 and a second affinity for a fixed and partially complementary nucleic acid 190 functioning as an anchor. The aptamer 180 has a higher affinity for the analyte 185 than for the complementary nucleic acid strand 190 functioning as the anchor. In the absence of the analyte 185, the aptamer 180 of the bistable switch 175 spends a majority of time bound to the complementary nucleic acid 190 function as the anchor, which stabilizes the bistable switch 175 is in the orientation shown in the left panel of the bottom inset of FIG. 2. Alternately, in the presence of the analyte 185, the aptamer 180 binds to the analyte 185 with a high affinity and is thus excluded from binding to the complementary nucleic acid strand 190. The aptamer 180 and analyte 185 complex further inhibits blunt-ended DNA stacking on the end 170 of the molecular barcoded bi-stable switch 140 having the bistable switch 175. Thus, in the presence of the analyte 185, the bistable switch 175 tends toward the orientation shown in the right panel of the bottom inset of FIG. 2. The bistable switch 175 includes two protein portions as a status identifier 195, where the position and spacing of the protein portions relative to the remainder of the molecular barcoded bi-stable switch 140 changes relative to the orientation of the aptamer 180 bound with analyte 185 and aptamer 180 bound with the complementary nucleic acid strand 190. In this manner, the status identifier 195 provides an indication of when the aptamer 180 (i.e., the binding material) is bound to the analyte 185 and when the aptamer 180 is bound to the complementary nucleic acid 190.

Figure 3A:
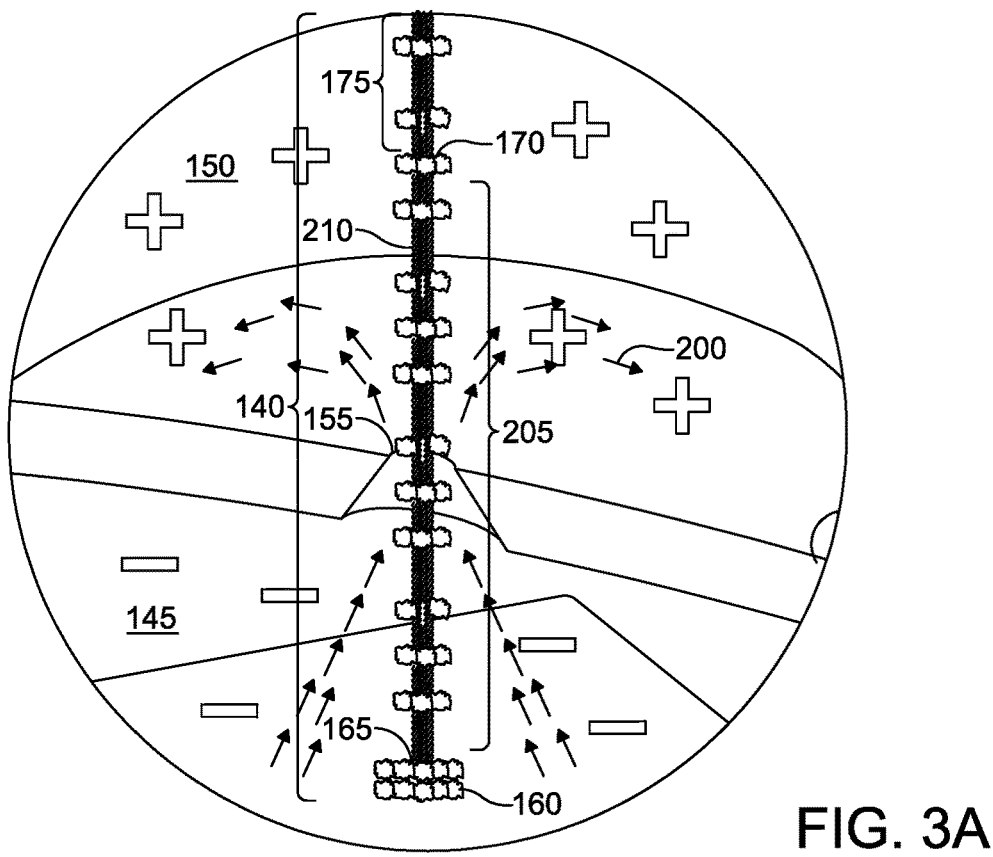
FIGS. 3A and 3B depict at least a portion of the molecular barcoded bi-stable switch being reversibly electrophoretically drawn through a pore of the sensor.
Figure 3B:
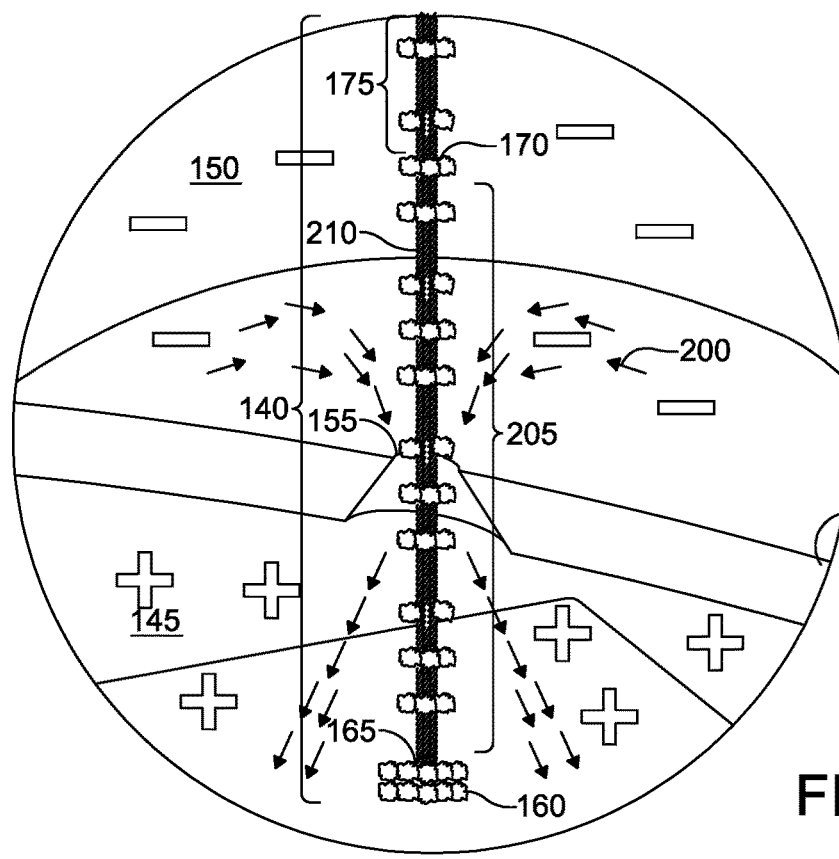
Figure 4:
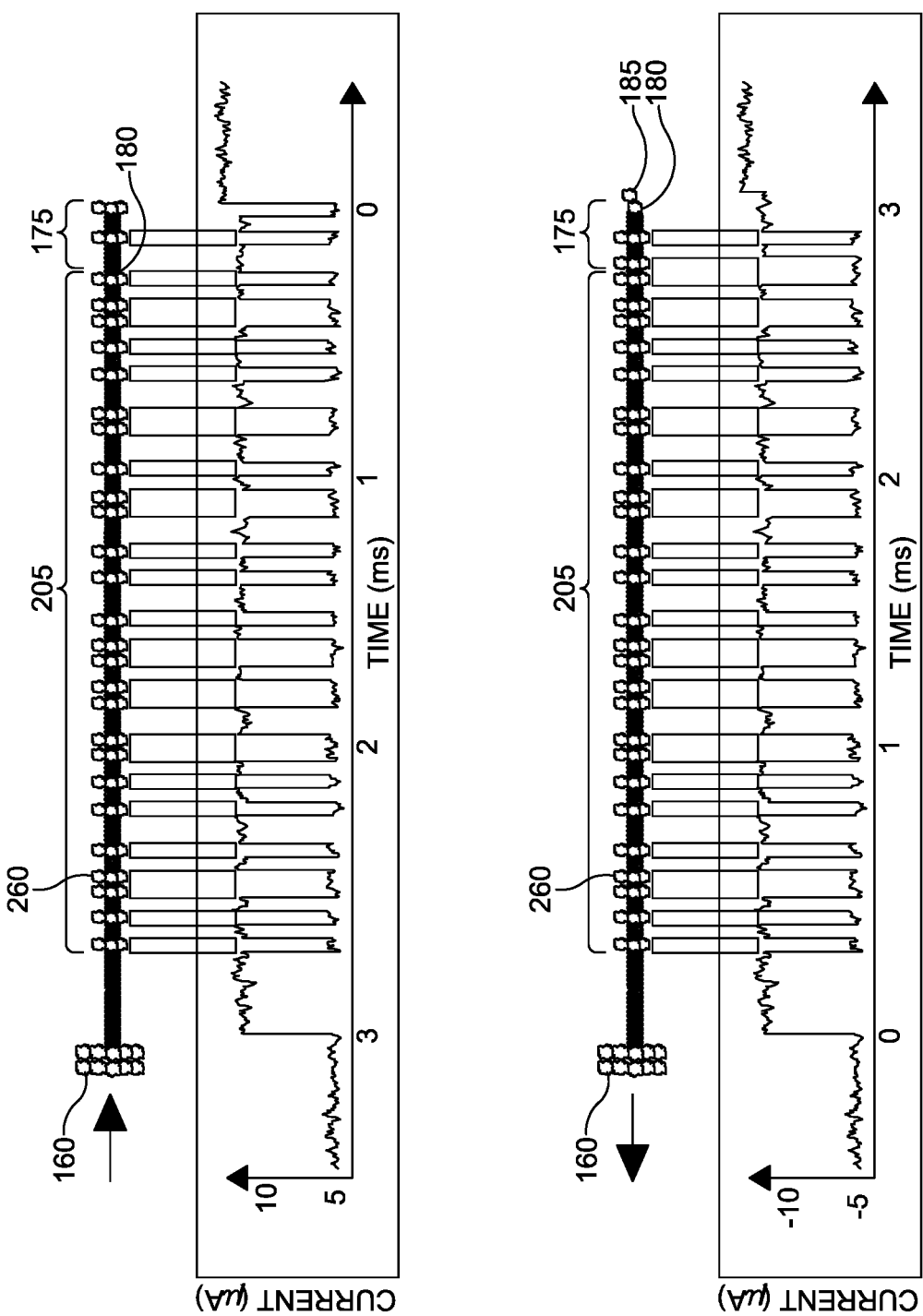
FIG. 4 depicts a way of ascertaining a barcode and an indication of a status identifier of the molecular barcoded bi-stable switch.

FIGS. 3A and 3B and the two panels of FIG. 4 show how the sensor 105 can ascertain whether the bistable switch 175 of a single molecular barcoded bi-stable switch 140 has encountered an analyte 185 to which the aptamer 180 is directed. At the beginning of a scan cycle for the presence of analyte 185 in a fluid sample, the molecular barcoded bi-stable switch 140 can be electrophoretically drawn out through the nano-pore 155 by a few microamps of current 200 passing through the pore 155, as shown in FIG. 3A. The molecular barcoded bi-stable switch 140 shown includes a barcode 205 formed by a series of proteins bound to a specific portions of a nucleic acid body 210. As each band of protein in the barcode 205 along the length of the body 210 of the barcoded bi-stable switch 140 passes through the pore it attenuates a flow of current 200 consistent with the Coulter Principle. The barcode 205 proteins provide a spatial pattern unique to the molecular barcoded bi-stable switch 140. Collectively, the proteins forming the barcode 205 spatial pattern produce a current "ripple" which is recorded with a microammeter. The current "ripple" signal can be decoded using algorithms and circuitry similar to those used in ordinary linear barcode scanners. Accordingly, the barcode 205 and the indication of the status identifier 195 of a particular molecular barcoded bi-stable switch 140 can be recorded. In certain embodiments, the barcode 205 can be formed as part of the body 210, where the body 210 is configured as an elongate member that includes a spatial pattern of large and small diameters of an intermediate portion of the elongate member, in lieu of comprising one or more separate molecules attached to the intermediate portion of the elongate member (not shown).

As the molecular barcoded bi-stable switch 140 is fully extended through the pore 155, the stopper 160 reaches the pore 155 and produces a steady low flow of current 200. At this point, a brief dwell period begins to allow the molecular barcoded bi-stable switch 140 to equilibrate to the chemical environment outside the nano-pore cell and encounter any analyte 185 present in an exterior 150 liquid volume. After the dwell period, a reverse current 200 is applied to the cell 135, as shown in FIG. 3B, and the molecular barcoded bi-stable switch 140 is pulled back through the nano-pore 155 and again scanned to read the indication of the status identifier 195 and the barcode 205. In certain embodiments, the molecular barcoded bi-stable switch 140 can be constructed without a stopper 160, where the molecular barcoded bi-stable switch 140 can be mixed directly into a liquid sample volume that may contain the analyte 185, and can then be scanned by passage through the nano-pore 155 and into the cell 135 in a continuous (non-reversing) fashion.

In the particular example shown in FIGS. 3A and 3B, the bi-stable switch 175 along with the status identifier 195 flipped from absent (no analyte during the outbound scan) to present (analyte bound during the inbound scan). The result in this example indicates that the molecular barcoded bi-stable switch 140 experienced a higher concentration of analyte 185 in the exterior 150 of the nano-pore cell 135. Note that a large number of scans like this can be averaged to precisely determine concentration of a given analyte 185.

As further shown in the panels of FIG. 4, the barcode 205 includes a "2 of 5 interleaved" pattern encoding a fixed 6 digit decimal ID number that is assigned to the molecular barcoded bi-stable switch 140. In addition to the ID number, the signal from the barcode 205 can include a signal from the status identifier 195 representative of the bi-stable switch 175 orientation and the indication of whether the aptamer 180 is bound with the analyte 185. When using a 6 digit decimal ID number, for example, there can be up to 1 million unique types of molecular barcoded bi-stable switch 140 employed, each one capable of detecting its own unique analyte 185 (e.g., medication, nutrient, hormone, neurotransmitter, etc.). Since the barcodes 205 representing the 1 million types of ID numbers can easily be distinguished in solution, a single nano-pore cell 135 can therefore scan a mixture of all 1 million molecular barcoded bi-stable switches 140, or a plurality of cells 135 and ammeters can be employed.

The present technology also includes using a molecular barcoded bi-stable switch 140 without a stopper 160 and/or a molecular barcoded bi-stable switch 140 without the bi-stable switch 175 portion. Such embodiments of the molecular barcoded bi-stable switch 140 can be scanned using the nano-pore cell 135 as described in a continuous fashion. An example application for such molecular barcoded bi-stable switches 140 includes using one or more of these molecular barcoded bi-stable switches 140 as a chemical taggant to be added to a material, solution, or fluid, such as food, drink, various chemicals, petroleum, ink, paper, perfume, medication, various controlled substances, explosives, etc. to allow easy testing of tagged items for qualities such as lot number, concentration, etc. The material, solution, or fluid can be scanned by electrophoretically by drawing the molecular barcoded bi-stable switch 140 through a device having a nano-pore 155 using a few microamps of current 200. For example, as each band of protein along the length of the barcode 205 in the molecular barcoded bi-stable switch 140 passes through the pore 155, the band attenuates the flow of current 200 consistent with the Coulter Principle. Collectively this pattern of bands produces a current "ripple" which is recorded with a micro-ammeter. This signal can be decoded using algorithms and circuitry similar to those used in ordinary linear barcode scanners. Accordingly, the identity and switch status of a particular molecular barcoded bi-stable switch 140 can be recorded.

Figure 5:
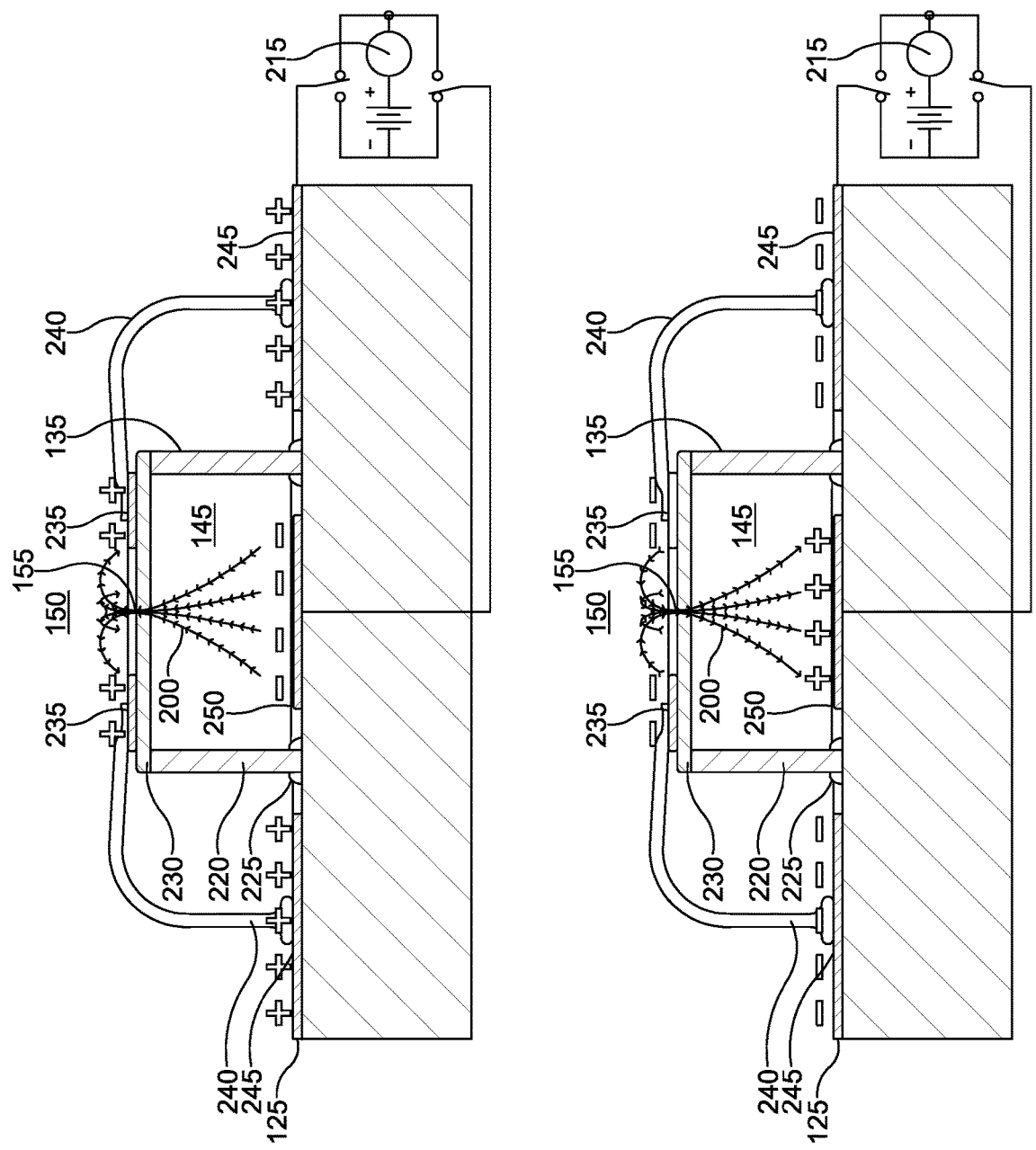
FIG. 5 depicts cross-sectional schematics of the sensor where at least a portion of the molecular barcoded bi-stable switch is reversibly electrophoretically drawn through a pore of the sensor.

FIG. 5 shows a cross-section of an embodiment of the nano-pore cell 135 along with a simplified electrical schematic of a micro-ammeter circuit 215. The nano-pore cell 135 can be positioned on the surface 125 of the sensor 105 and can include a cell wall 220, a sealant 225, and a nano-pore plate 230 including the pore 155, which can all be formed of materials that are good electrical insulators to prevent current 200 from leaking between the interior 145 and the exterior 150 of the cell 135. One or more exterior electrodes 235, shield wire 240, and one or more ground planes 245 are all securely fused together to collectively form a Faraday cage, which reduces electrical background noise. Isolated inside the cell 135 is the interior electrode 250. This arrangement leaves the nano-pore 155 itself as the sole path for current 200 to flow between the interior electrode 250 and the exterior electrodes 235. In this embodiment, all the conductive materials (e.g., interior electrode 250, exterior electrodes 235, ground planes 245) can be formed by a thin layer of gold plated onto the respective insulating silicon substrates (e.g., surface 125 of the sensor 105, nano-pore plate 230). The shield wire 240 can be a 17 μm diameter gold wire electrically connected to both the ground planes 245 and the exterior electrodes 235 using a conventional thermosonic bonder.

In the top panel of FIG. 5, the exterior electrodes 235 are positively charged which causes a negatively charged molecular barcoded bi-stable switch 140 to be drawn outward through the nano-pore 155. After a predetermined time interval, the micro-ammeter circuit 215 is reversed causing the molecular barcoded bi-stable switch 140 to be drawn back inward through the nano-pore 155, as shown in the bottom panel of FIG. 5.

Figure 6:
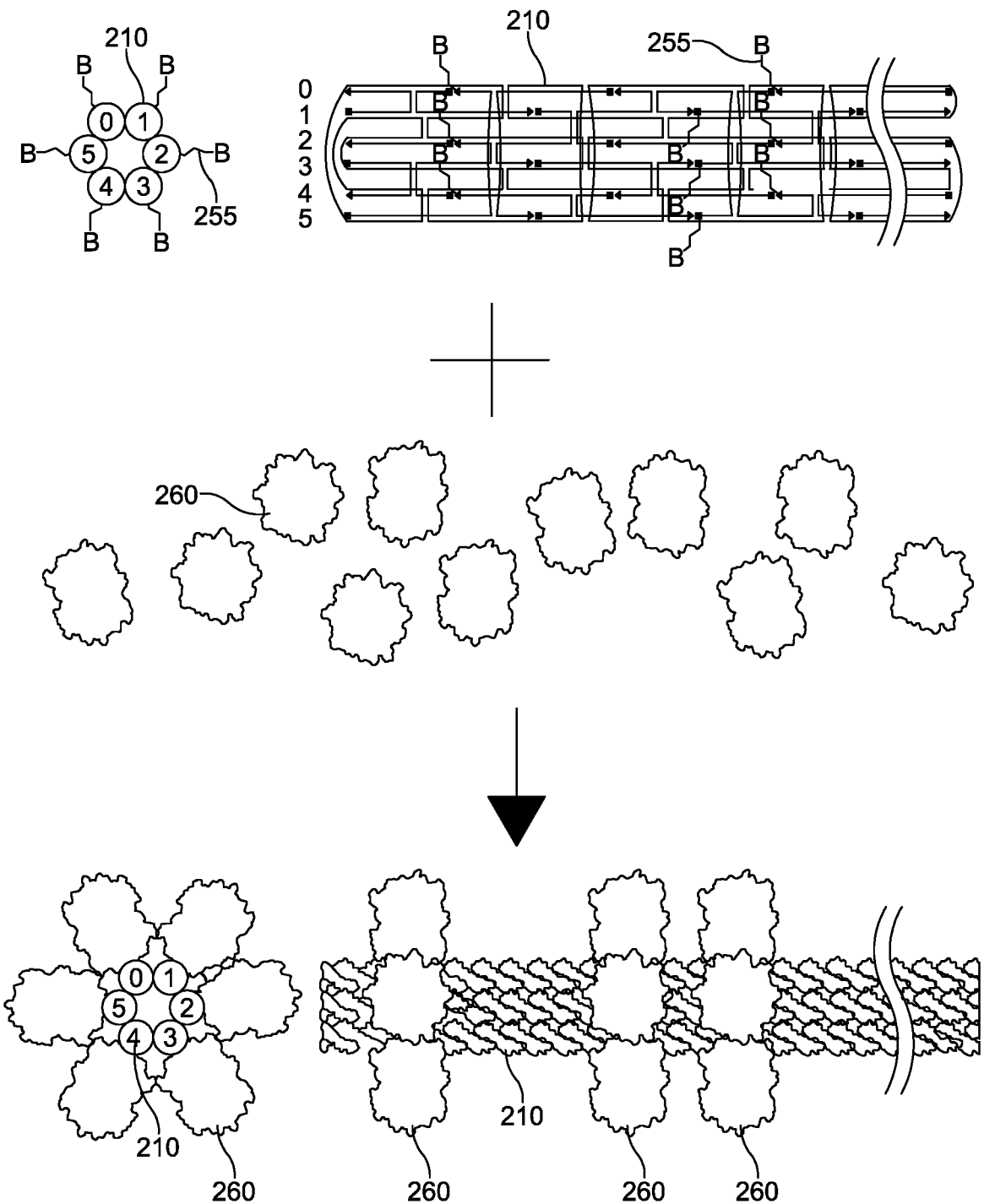
FIG. 6 depicts a way to make a molecular barcoded bi-stable switch, including the use of DNA origami.
Figure 7:
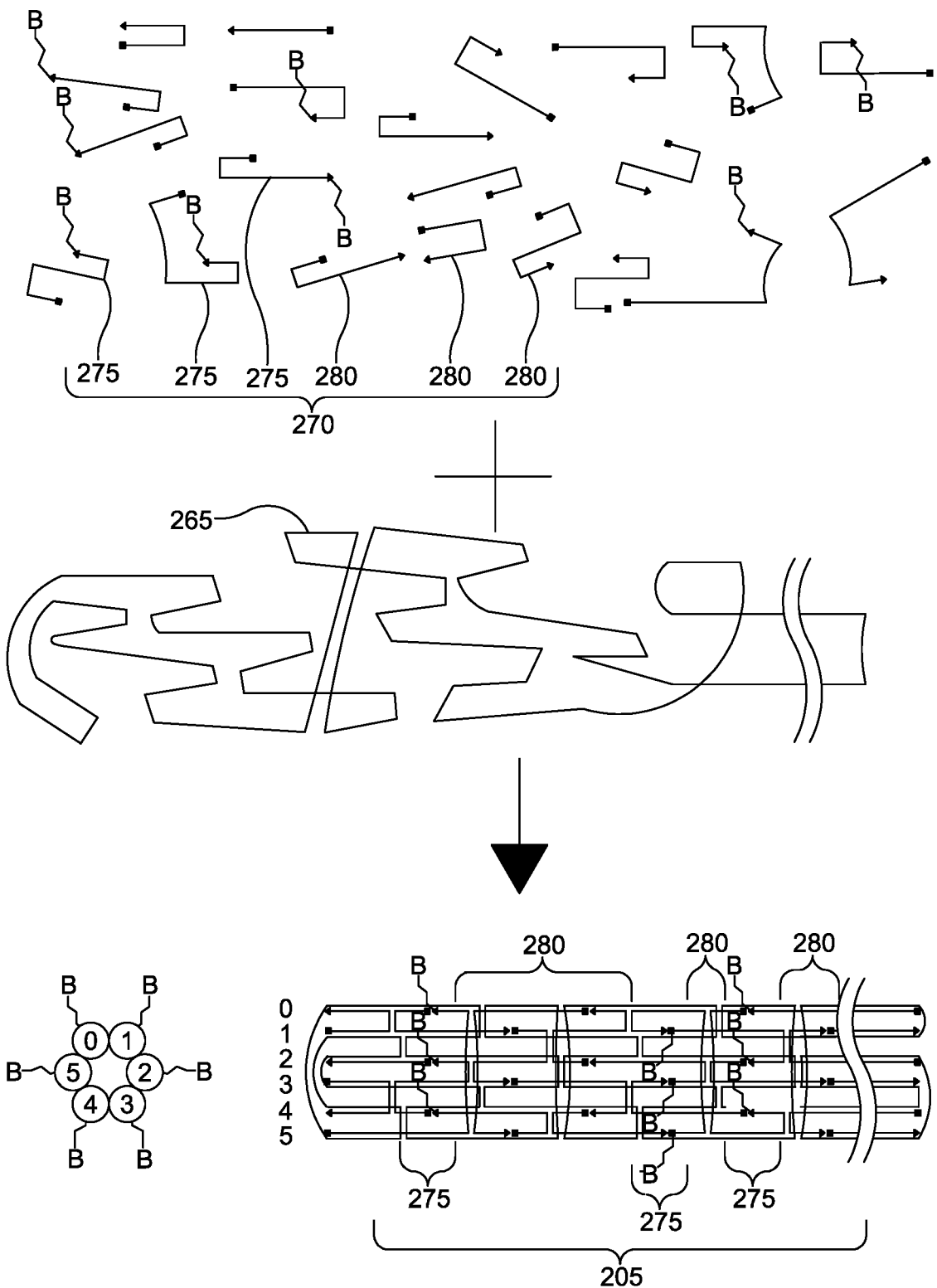
FIG. 7 depicts further details of making the molecular barcoded bi-stable switch.

FIGS. 6 and 7 show an embodiment of the structure of the molecular barcoded bi-stable switch 140 and a schematic for a process used to manufacture the molecular barcoded bi-stable switch 140. In FIG. 6, the body 210 of the molecular barcoded bi-stable switch 140 is a nucleic acid nanostructure comprised of 6 parallel strands of DNA that can be created using a process called DNA origami (shown in greater detail in FIG. 7). Along the length of the body 210 is a designated pattern of biotinylated sites 255. Monovalent streptavidin proteins 260 are attached to these biotinylated sites 255 which collectively form the current blocking "bars" in the barcode 205, as described. An example of fabricating such a structure is provided in "A monovalent streptavidin with a single femtomolar biotin binding site" by Howarth M, Chinnapen D J, Gerrow K, Dorrestein P C, Grandy M R, Kelleher N L, El-Husseini A, Ting A Y *Nat Methods.* 2006 Apr. 3(4):267-73. Note that while in one bar in the barcode 205 is comprised of six streptavidin proteins 260 bound to six biotinylated sites 255 positioned about the perimeter of the body 210 formed of the 6 parallel strands of DNA, experimental evidence shows that even a single streptavidin protein 260 provide a detectable change in current 200 as it passes through the pore 155. An example of such detection is provided in "Selective Detection and Quantification of Modified DNA with Solid-State Nanopores" by Carlsen A T, Zahid O Z, Ruzicka J A, Taylor E W, Hall A R *Nano Lett.,* 2014, 14 (10), pp 5488-5492. However, to ensure a more robust signal, at least three streptavidin proteins 250 can be used per bar of the barcode 205, where 6 streptavidin proteins are used per bar in FIG. 6.

FIG. 7 shows a schematic view of the construction of the body 210 of the molecular barcoded bi-stable switch 140 using DNA origami. In general, the DNA origami process is well documented and has been used to form various complex structures, including structures more complex than the primarily linear body 210 used here. An example using DNA origami to form a nucleic acid structure, such as the body 210 of the molecular barcoded bi-stable switch 140, is provided in "Cryo-EM structure of a 3D DNA-origami object" by Bai X C, Martin T G, Scheres S H W, Dietz H *PNAS* 2012 109 (49) 20012-20017. The body 210 of the molecular barcoded bi-stable switch 140 can be comprised of a continuous single-stranded plasmid loop of DNA serving as a scaffold strand 265 which runs continuously throughout the structure of the body 210, arranged in a parallel repeating pattern as loosely shown in the middle panel of FIG. 7. This scaffold strand 265 is folded and securely stitched into its final shape by engulfing it with an excess of short oligonucleotides termed staple strands 270. The necessary sequence of these staple strands 270 can be calculated using an open source software called caDNAno. An example of the process is provided in "Rapid prototyping of 3D DNA-origami shapes with caDNAno" by Douglas S M, Marblestone A H, Teerapittayanon S, Vazquez A, Church G, Shih W *Nucl. Acids Res.* (2009) 37 (15): 5001-5006. Staple strands 270 at desired barcode 205 "bar" locations 275 can be synthesized with a triethyleneglycol (TEG) spacer and biotin molecule attached to their 3' termini to provide the biotinylated sites 255. In other embodiments, these staple strands 270 can be biotinylated using various 5', 3', or internal attachment chemistry. Staple strands 270 at desired barcode 205 "space" locations 280 between the bars of the barcode 205 can use staple strands 270 that are not biotinylated. In some embodiments, once the structure of the body 210 is properly folded and purified, these staple strands 270 can be ligated to increase thermal stability and shelf life of the molecular barcoded bi-stable switch 140.

FIGS. 8-13 depict further embodiments of the molecular barcoded bi-stable switch. These embodiments can include particular configurations of the following additional aspects, which are based on functionalities of various molecular barcoded bi-stable switches as previously presented herein. First, the molecular barcoded bi-stable switch can be configured to operate using cooperative binding of the analyte, where in a particular embodiment the binding material and the anchor cooperatively bind the analyte. Second, the bistable switch can be stabilized in the absence of bound analyte by a stabilizing element or catch strand. Third, the barcode portion of the molecular barcoded bi-stable switch can be formed using wide and narrow sections of the body or elongate member, such as wide and narrow sections of DNA, rather than the examples of streptavidin protein attachments to biotinylated sites on the elongate member of the body. Fourth, the molecular barcoded bi-stable switch can include where the status identifier operates via a hinged action as opposed to the flipping or reversal of orientation depicted in FIG. 2. It is understood that these aspects can be used in conjunction with other embodiments described herein and various combinations of molecular barcoded bi-stable switches having various operating characteristics and configurations can be employed in various sensors, methods, and systems of the present technology. Such molecular barcoded bi-stable switches can be configured for individual analytes and/or can be configured for redundant detection of the same analyte, albeit using different configurations, including different bodies, barcodes, stoppers, and bi-stable switch modalities. For example, certain bi-stable switch modalities may be optimized for certain analytes as well as derivatives of certain analytes.

Figure 8:
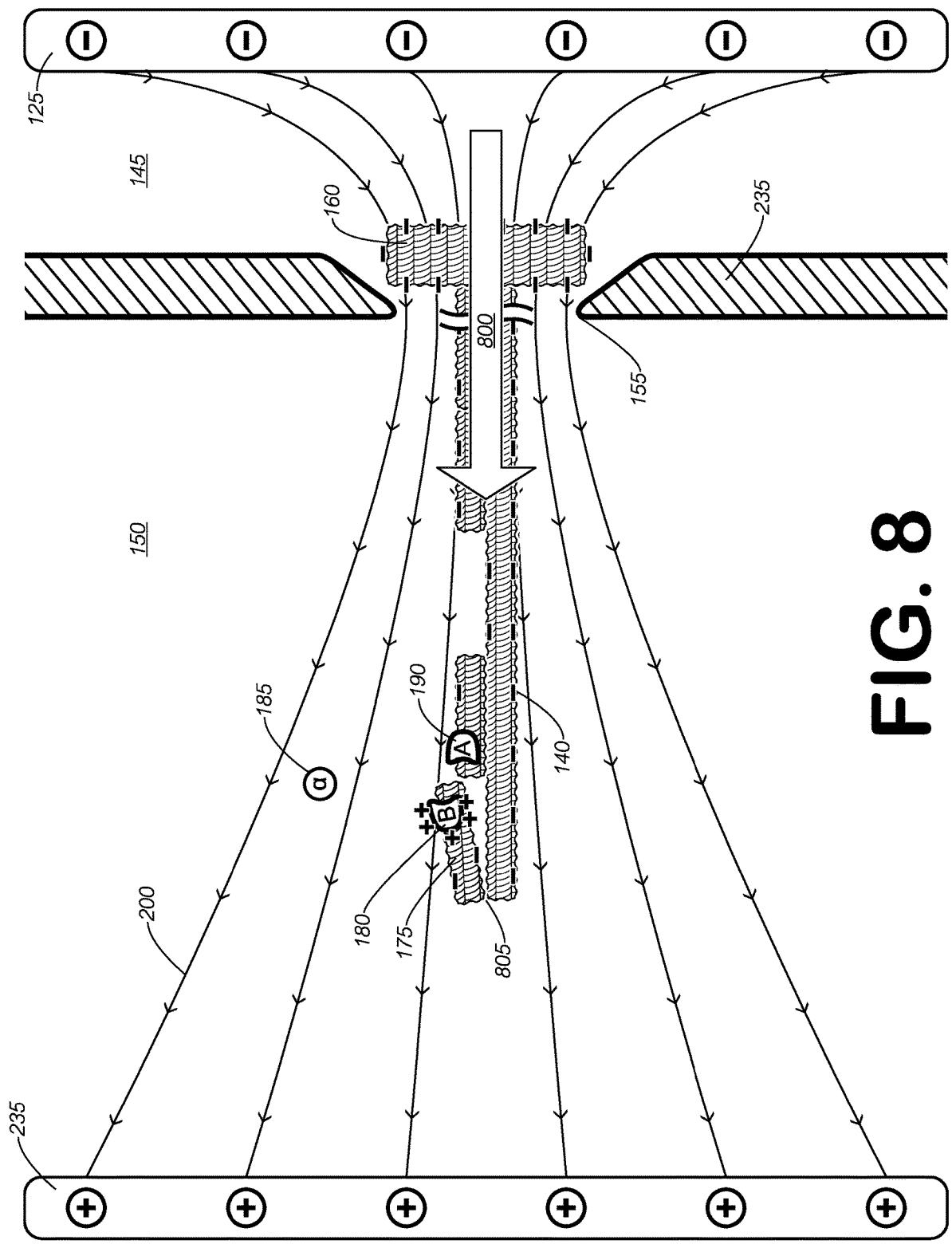
FIG. 8 depicts another embodiment of the molecular barcoded bi-stable switch passing through the pore of the sensor.

FIG. 8 shows an embodiment of a molecular barcoded bi-stable switch 140 initially scanning into the nano-pore 155 from the first volume 145 to the second volume 150. The stopper 160 can prevent the molecule from freely diffusing into the second volume 150 through the pore 155. Since opposite charges are attracted to each other, the electrical field 200 causes the negatively charged bi-stable switch 140 to be electrophoretically drawn out 800 toward the positively charged electrode 235. Note that while the overall charge on the molecular barcoded bi-stable switch 140 is negative, one minor region of the binding material bears a positive charge, which can be configured in a similar fashion as described for the aptamer 180 having an affinity for the analyte 185. Also note the presence of free analyte 185 in solution in the second volume 150.

Figure 9:
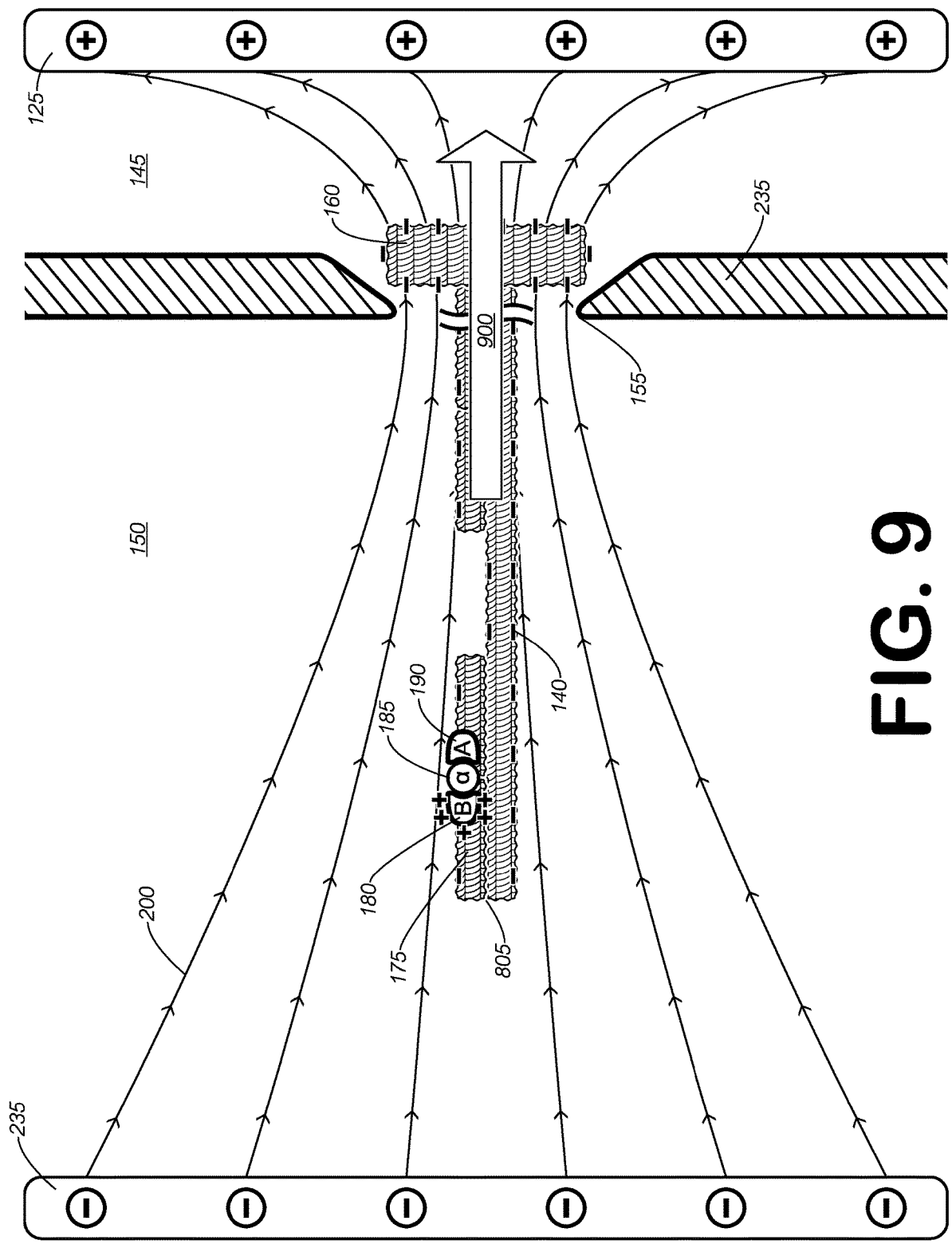
FIG. 9 depicts where the molecular barcoded bi-stable switch of FIG. 8 encounters an analyte.

FIG. 9 shows a scenario where the analyte 185 is present in solution; in this case the analyte 185 can cooperatively bind to both the binding material 180 and the anchor 190, where as shown the analyte 185 is effectively sandwiched therebetween. It is noted, however, that cooperative binding can operate in other orientations and ways. The cooperative binding securely locks the status identifier 175 in a closed or analyte-bound state; c.f. FIGS. 8 & 9. The electrical field 200 can then be reversed causing the overall negatively charged molecule 140 to now be attracted to the positively charged electrode 125, where the whole molecule 140 is then drawn in the opposite direction 900 in through the nano-pore 155.

Figure 10:
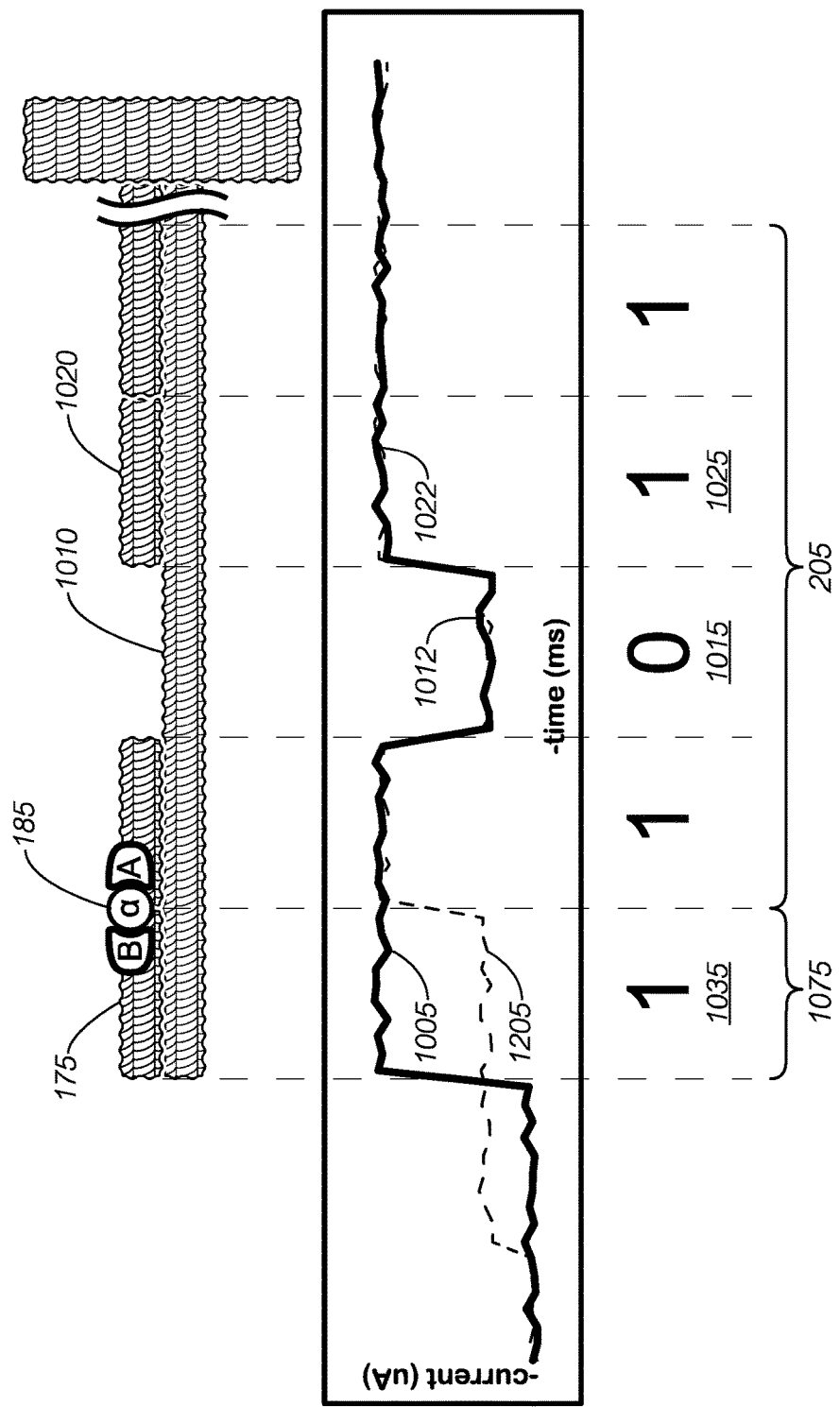
FIG. 10 depicts detection of the molecular barcoded bi-stable switch of FIG. 8 when bound with the analyte.

FIG. 10 shows a resulting current signature 1005 of the molecular barcoded bi-stable switch 140 in the closed or analyte-bound state (indicating the presence of the analyte 185) as the molecular barcoded bi-stable switch 140 moves in through the nano-pore 155 (shown in FIG. 9). Narrow regions 1010 of the molecular barcoded bi-stable switch 140 occlude less of the nano-pore 155 when passing through, thereby resulting in a lower resistance 1012 to the current flowing through the pore 155. This in turn can be interpreted as a digital "zero" 1015 in the overall barcode signal. Inversely, the wider regions 1020 occlude more of the nano-pore 155, and thus result in a higher resistance 1022 to the current, which in turn is interpreted as a digital "one" 1025. The status identifier 175 can also be locked closed by the presence of the analyte 185, where the cross-section of which is approximately equal to that of the wider sections of the barcode 1020. This in turn means the resulting current level 1005 at the status identifier 175 is interpreted as a digital "one" 1035. Overall, the four binary numbers 205 shown here can be part of the barcode region identifying the molecule, and the final binary number 1075 indicates the molecular switch status; i.e., presence or absence of bound analyte.

Figure 11:
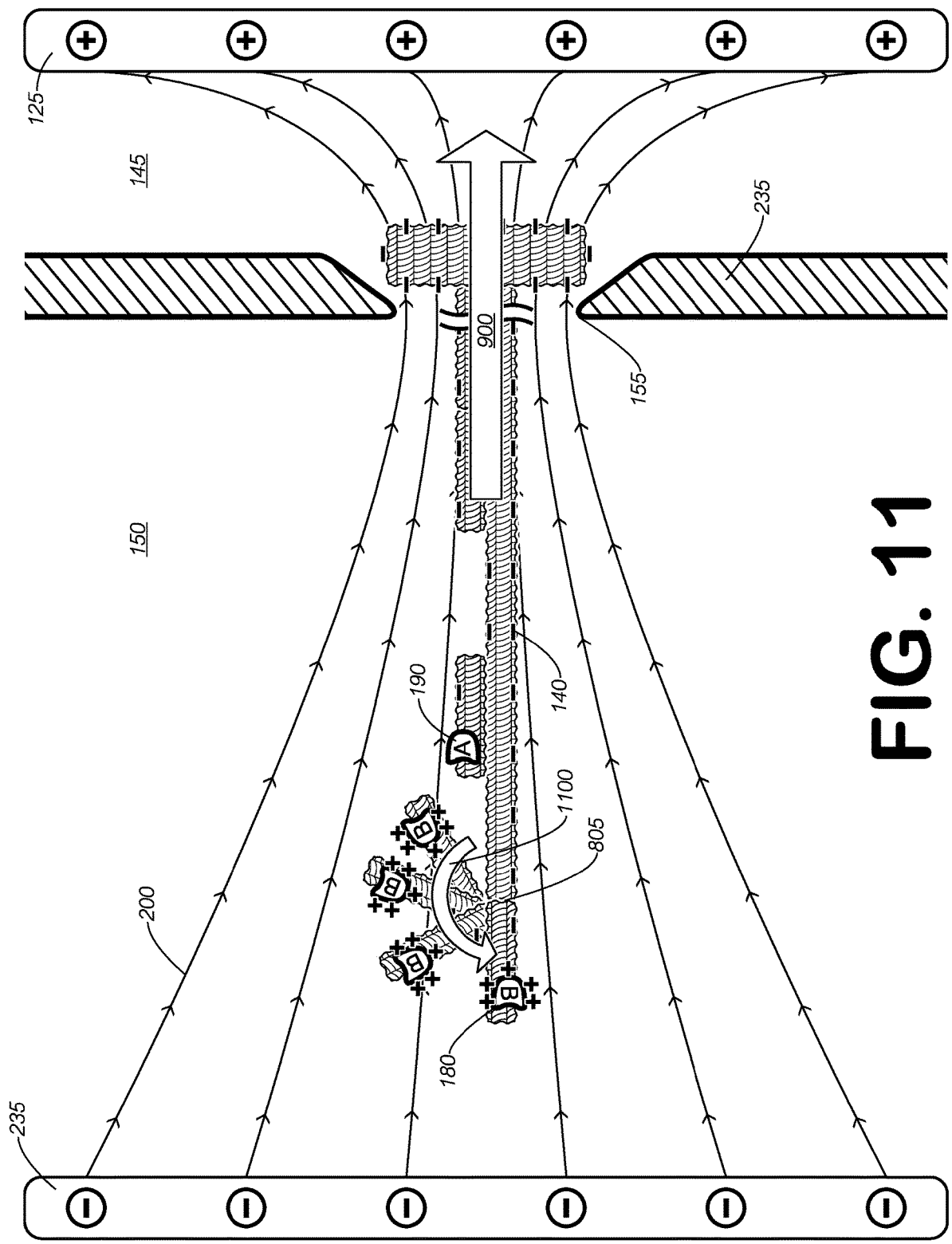
FIG. 11 depicts where the molecular barcoded bi-stable switch of FIG. 8 does not encounter the analyte.

FIG. 11 shows a scenario in which the analyte is absent from solution; in this case, the binding material 180 and the anchor 190 have little or no affinity for each other, allowing the status identifier 175 to swing freely on its hinge 805. Just as in FIG. 9, the electrical field 200 can be reversed causing the overall negatively charged molecular barcoded bi-stable switch 140 to now be attracted to the positively charged electrode 125, causing the molecular barcoded bi-stable switch 140 to be drawn inward 900 through the nano-pore 155. Unlike FIG. 9, however, here the analyte is absent and the status identifier 175 is free to swing on its hinge 805. The minor region bearing a positive charge 180 is pulled toward the negatively charged electrode 235. This causes the status identifier 175 to swing open 1100 as the molecular barcoded bi-stable switch 140 is pulled inward 900 through the nano-pore 155.

Figure 12:
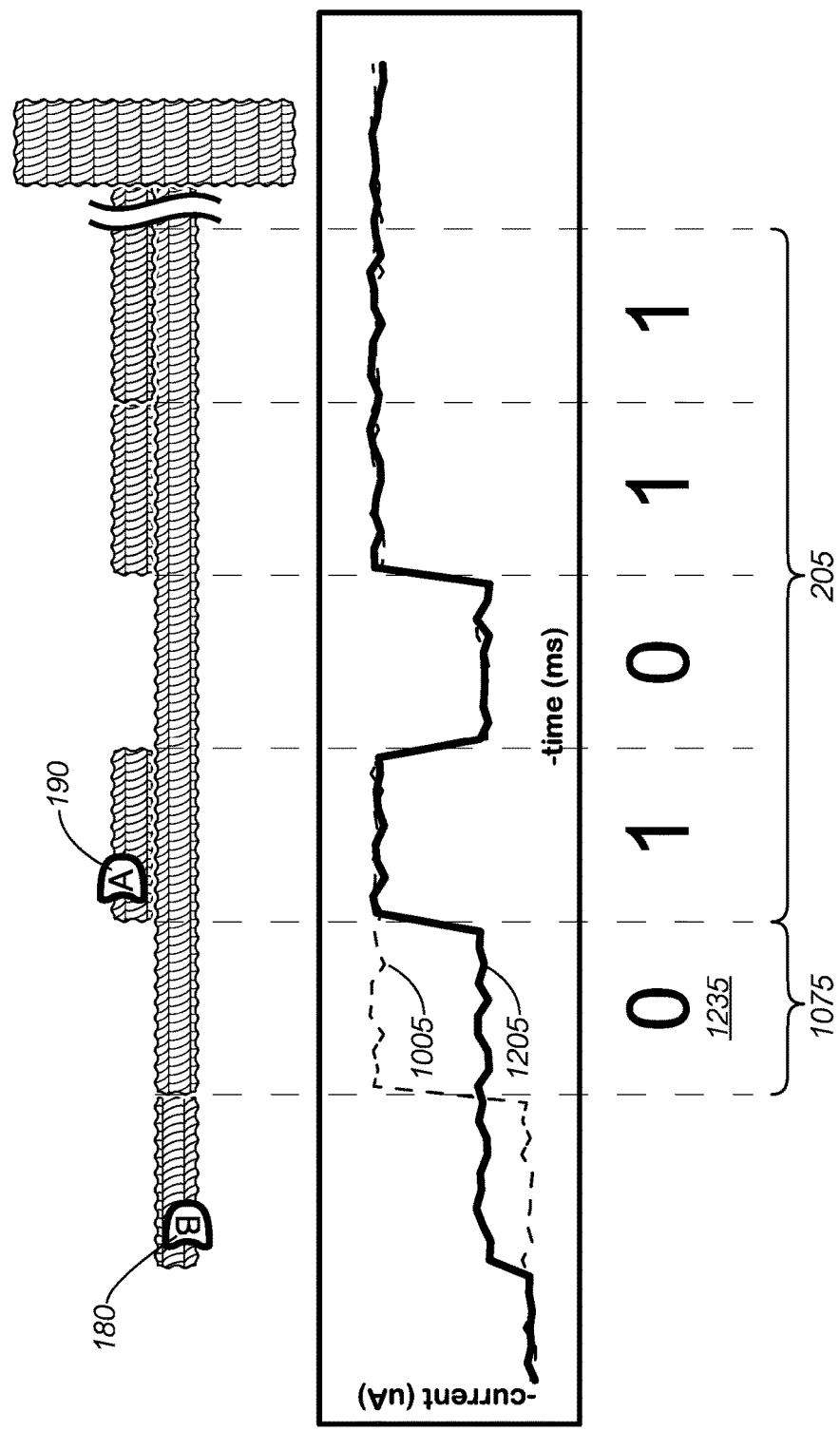
FIG. 12 depicts detection of the molecular barcoded bi-stable switch of FIG. 8 when not bound with the analyte.

FIG. 12 shows a resulting current signature 1205 of the molecular barcoded bi-stable switch 140 in its closed state (indicating the absence of the analyte) as it migrates in through the nanopore (shown in FIG. 11). In this example, the status identifier 175 is swung open in the absence of the analyte, which means its cross-section is approximately equal to that of the narrow sections of the barcode 1010. This in turn can permit the resulting current level 1205 to be interpreted as a digital "zero" 1235. Otherwise, the barcode region 205 can be identical to the one shown in FIG. 10.

Figure 13:
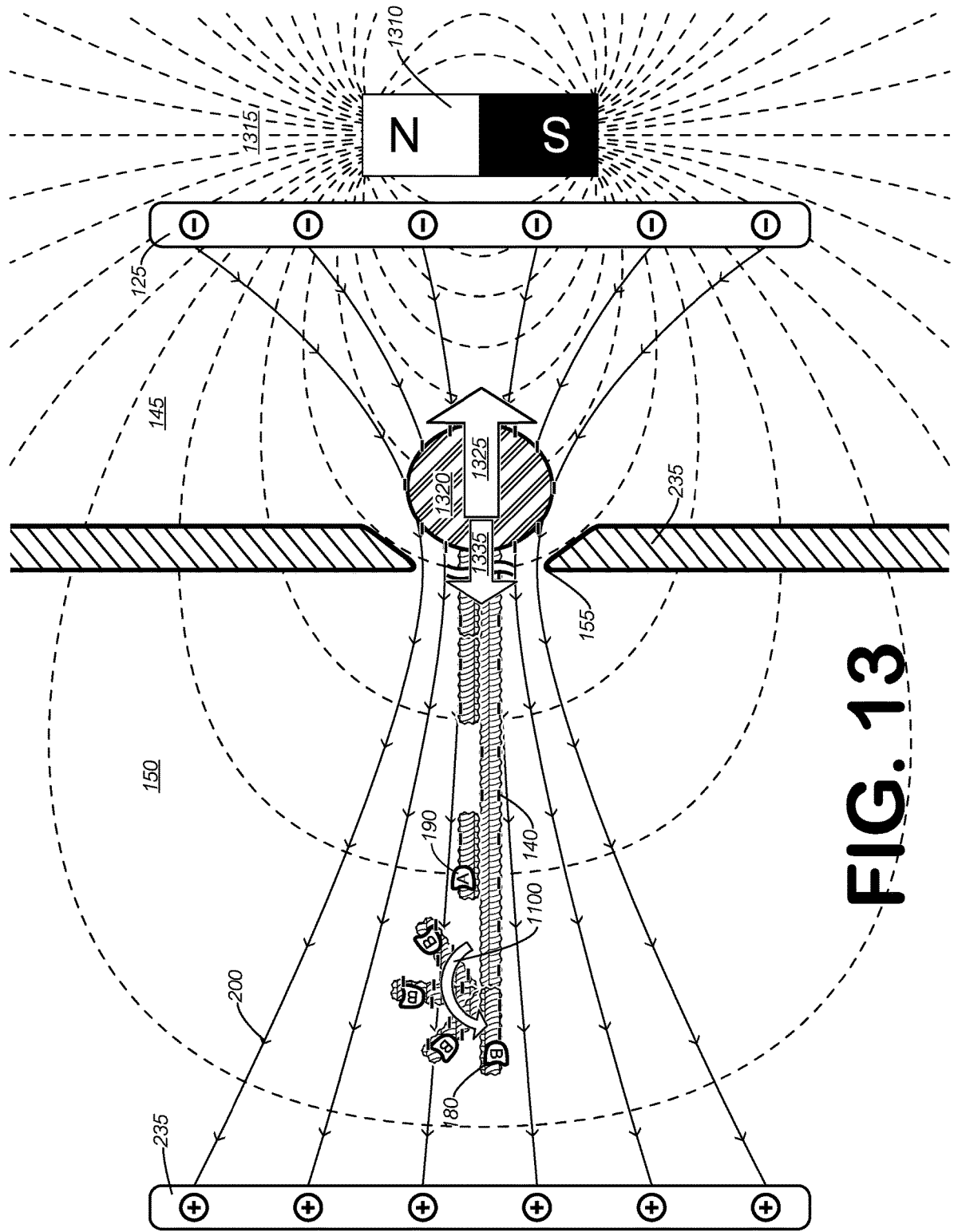
FIG. 13 depicts yet another embodiment of the molecular barcoded bi-stable switch passing through the pore of the sensor.

FIG. 13 shows an embodiment where the stopper includes a magnetic bead 1320 that has a dimension unable to pass through the nano-pore 155. In this embodiment, the current 200 flowing through the nano-pore 155 does not need to be reversed in order for the molecular barcoded bi-stable switch 140 to be scanned as well as retracted from the pore 155. In this scenario, two opposing forces are acting on the molecular barcoded bi-stable switch 140—the first force 1335 is the electrophoretic attraction between the negatively charged molecular barcoded bi-stable switch 140 and the positively charged electrode 235 (e.g., as shown in FIG. 8) and the second force 1325 is applied via a magnetic field 1315 from a permanent magnet 1310 (as shown) or induced using a coil. The strength of one or both of these two forces 1325, 1335 can be modulated in order to tune and control of a speed and/or a position of the molecular barcoded bi-stable switch 140 as it passes into or out of the nano-pore 155.

Figure 14:
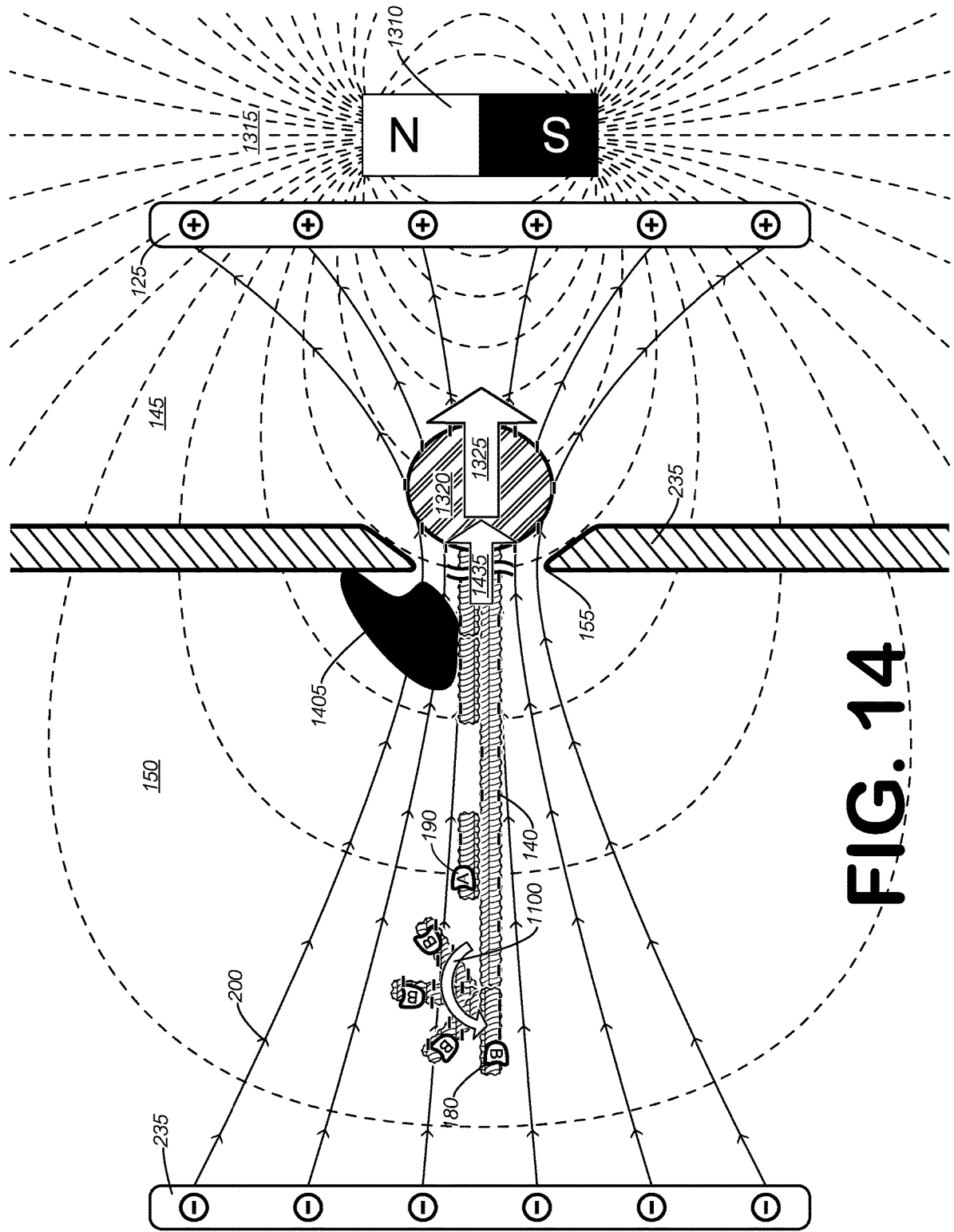
FIG. 14 depicts where the current is reversed for the molecular barcoded bi-stable switch of FIG. 13 so that the molecular barcoded bi-stable switch passes back through the pore of the sensor, where passage of the molecular barcoded bi-stable switch can clear an obstruction occluding or at least partially occluding the pore.

FIG. 14 shows an embodiment similar to FIG. 13, except that in this case the current is reversed, and thus the magnetic 1325 and electrophoretic 1435 forces now combine to provide a combined force. This can be useful to clear a molecular barcoded bi-stable switch 140 that has become fouled by unwanted protein 1405 (or other detritus) introduced in sample fluid(s) tested for analyte 185, where the molecular barcoded bi-stable switch 140 is no longer free to move through the nano-pore 155. Both forces 1325, 1435 in combination can help clear the nano-pore 155 of unwanted protein 1405 that may partially or fully occlude the nano-pore 155 and interfere with passage of the molecular barcoded bi-stable switch 140 therethrough. In this way, the nano-pore can be cleared and made available for subsequent scans. Multiple passages of the molecular barcoded bi-stable switch 140 using the combined forces 1325, 1435 through the nano-pore 155 can be preformed to dislodge unwanted protein 1405 or other detritus adjacent the pore 155 to refresh the sensor and maximize function thereof.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A molecular barcoded bi-stable switch for an analyte comprising:
   a body including an elongate member;
   a barcode;
   a stopper having a first dimension relative a diameter of the elongate member, the barcode having a second dimension relative to the diameter of the elongate member, the first dimension greater than the second dimension; and
   a bi-stable switch including a binding material, an anchor, and a status identifier, wherein the binding material, the anchor, and the analyte cooperatively bind together, the status identifier providing an indication when the analyte is cooperatively bound with the binding material and the anchor, the indication provided with the status identifier coupled to the body.

2. The molecular barcoded bi-stable switch of claim 1, wherein the binding material has a first affinity for the analyte and the anchor has a second affinity for the analyte.

3. The molecular barcoded bi-stable switch of claim 2, wherein the binding material and the anchor cooperatively bind the analyte with a third affinity, the third affinity being greater than the first affinity and greater than the second affinity.

4. The molecular barcoded bi-stable switch of claim 2, wherein the binding material has a first affinity for a first epitope of the analyte and the anchor has a second affinity for a second epitope of the analyte.

5. The molecular barcoded bi-stable switch of claim 1, wherein the analyte is sandwiched between the binding material and the anchor when the analyte is cooperatively bound with the binding material and the anchor.

6. The molecular barcoded bi-stable switch of claim 1, wherein the stopper includes one of a particle and a bead.

7. The molecular barcoded bi-stable switch of claim 6, wherein the one of the particle and the bead provides the first dimension.

8. The molecular barcoded bi-stable switch of claim 1, wherein the stopper includes a magnetic component.

9. The molecular barcoded bi-stable switch of claim 1, wherein the stopper includes a magnetic bead.

10. The molecular barcoded bi-stable switch of claim 1, wherein the molecular barcoded bi-stable switch includes a portion that is electrically charged.

11. The molecular barcoded bi-stable switch of claim 1, wherein the stopper includes a magnetic bead and the molecular barcoded bi-stable switch includes a portion that is electrically charged.

12. The molecular barcoded bi-stable switch of claim 1, wherein the body comprises a nucleic acid polymer.

13. The molecular barcoded bi-stable switch of claim 1, wherein the barcode comprises a plurality of molecules coupled to the body that provide a spatial pattern unique to the molecular barcoded bi-stable switch.

14. The molecular barcoded bi-stable switch of claim 1, wherein the barcode comprises a narrow region of the elongate member and a wide region of the elongate member, the narrow region having a diameter less than the wide region, the wide region having a diameter that is not wider than the diameter of the elongate member, and the narrow region and the wide region providing a spatial pattern unique to the molecular barcoded bi-stable switch.

15. The molecular barcoded bi-stable switch of claim 14, wherein the status identifier alters the spatial pattern when the binding material, the anchor, and the analyte cooperatively bind together.

16. The molecular barcoded bi-stable switch of claim 1, wherein the binding material and the anchor are independently a member selected from the group consisting of a receptor, an antibody, and an aptamer.

17. The molecular barcoded bi-stable switch of claim 1, wherein the indication comprises a position change of the status identifier relative to a remainder of the barcode when the binding material, the anchor, and the analyte cooperatively bind together.

18. A sensor for detecting an analyte comprising:
    a molecular barcoded bi-stable switch for the analyte including:
      a body;
      a barcode; and
      a bi-stable switch including a binding material, an anchor, and a status identifier, wherein the binding material, the anchor, and the analyte cooperatively bind together, the status identifier providing an indication when the analyte is cooperatively bound with the binding material and the anchor, the indication provided with the status identifier coupled to the body;
    a first volume fluidly connected to a second volume by a pore, the molecular barcoded bi-stable switch disposed in one of the first volume and the second volume; and
    a first electrode in electrical communication with the first volume and a second electrode in electrical communication with the second volume, the pore permitting an electrical current to pass between the first volume and the second volume.

19. The sensor of claim 18, wherein the barcode is configured to change the electrical current when the barcode passes through the pore.

20. The sensor of claim 18, further comprising a plurality of the molecular barcoded bi-stable switches.

21. The sensor of claim 20, wherein the plurality of molecular barcoded bi-stable switches comprises a plurality of different molecular barcoded bi-stable switches each having a different barcode and each having a different binding material with a different first affinity for a different analyte.

22. The sensor of claim 18, further comprising:
    a plurality of the first volumes fluidly connected to a plurality of the second volumes by a plurality of pores;
    a plurality of first electrodes, a respective one of the first electrodes in electrical communication with a respective one of the first volumes, and a plurality of second electrodes, a respective one of the second electrodes in electrical communication with a respective one of the second volumes, a respective one of the pores permitting an electrical current to pass between the respective one of the first volumes and the respective one of the second volumes; and a plurality of the molecular barcoded bi-stable switches.

23. The sensor of claim 22, wherein the plurality of molecular barcoded bi-stable switches comprises a plurality of different molecular barcoded bi-stable switches each having a different barcode and each having a different binding material with a different first affinity for a different analyte, and different molecular barcoded bi-stable switches are disposed in one of the respective first volumes and the respective second volumes.

24. The sensor of claim 22, wherein one of the first volume and the second volume comprises about 1 nanoliter of a liquid.

25. The sensor of claim 18, wherein the molecular barcoded bi-stable switch further comprises a stopper.

26. The sensor of claim 25, wherein the stopper is configured to reduce the electrical current when the stopper at least partially occludes the pore.

27. A method of detecting an analyte comprising:
providing a sensor for detecting an analyte including:
a molecular barcoded bi-stable switch for the analyte including:
a body;
a barcode; and
a bi-stable switch including a binding material, an anchor, and a status identifier, wherein the binding material, the anchor, and the analyte cooperatively bind together, the status identifier providing an indication when the analyte is cooperatively bound with the binding material and the anchor, the indication provided with the status identifier coupled to the body;
a first volume fluidly connected to a second volume by a pore, the molecular barcoded bi-stable switch disposed in one of the first volume and the second volume; and
a first electrode in electrical communication with the first volume and a second electrode in electrical communication with the second volume, the pore permitting an electrical current to pass between the first volume and the second volume;
providing an electrical current through the pore to electrophoretically draw at least a portion of the molecular barcoded bi-stable switch from one of the first volume and the second volume through the pore to the other of the first volume and the second volume; and
detecting the analyte when the indication includes a position change of the status identifier relative to a remainder of the barcode when the binding material is bound to the analyte.

28. The method of claim 27, further comprising reading the barcode as the barcode passes through the pore.

29. The method of claim 27, further comprising reversing the electrical current through the pore to electrophoretically draw at least a portion of the molecular barcoded bi-stable switch to the one of the first volume and the second volume through the pore from the other of the first volume and the second volume.

* * * * *